(12) United States Patent
Marczyk et al.

(10) Patent No.: US 9,198,718 B2
(45) Date of Patent: *Dec. 1, 2015

(54) SURGICAL DEVICE WITH POWERED ARTICULATION WRIST ROTATION

(71) Applicant: Covidien LP, Mansfield, MA (US)

(72) Inventors: Stanislaw Marczyk, Stratford, CT (US); Russell Pribanic, Roxbury, CT (US); Yong Ma, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,148

(22) Filed: Feb. 17, 2015

(65) Prior Publication Data

US 2015/0157394 A1    Jun. 11, 2015

Related U.S. Application Data

(63) Continuation of application No. 13/668,346, filed on Nov. 5, 2012, now Pat. No. 8,968,312.

(60) Provisional application No. 61/560,456, filed on Nov. 16, 2011.

(51) Int. Cl.
*A61B 18/14* (2006.01)
*A61B 17/29* (2006.01)
(Continued)

(52) U.S. Cl.
CPC ............. *A61B 18/1445* (2013.01); *A61B 17/29* (2013.01); *A61B 2017/00314* (2013.01); *A61B 2017/00323* (2013.01); *A61B 2017/00398* (2013.01); *A61B 2017/00734* (2013.01); *A61B 2017/2903* (2013.01);
(Continued)

(58) Field of Classification Search
USPC .......................... 606/41, 45–52, 105–102, 34
See application file for complete search history.

(56) References Cited

U.S. PATENT DOCUMENTS 3,173,417 A    3/1965    Homer
3,443,448 A    5/1969    Coss
(Continued)

FOREIGN PATENT DOCUMENTS

EP    1690492 A1    8/2006
EP    1908390 A1    4/2008
(Continued)

OTHER PUBLICATIONS

European Search Report EP 12192814 dated Feb. 13, 2013.
(Continued)

*Primary Examiner* — Paula J Stice

(57) ABSTRACT

A surgical instrument for treating tissue, the instrument including a housing and a shaft with an articulating portion and an end effector. The surgical instrument including a first casing connected to and rotatable with the proximal end of said shaft with an internal frame housed within the first casing and a plurality of posts supported by the internal frame and connected on their distal ends to at least one drive wire, and connected on their proximal ends to a threaded shaft; and a second casing connected to the first casing and rotatable therewith, said second casing housing the threaded shafts. The surgical instrument includes a first electric motor driving a first gear interfacing with the threaded shafts such that a first pair of the plurality of threaded shafts rotate in the same direction and cause the articulating portion to articulate in a first plane.

1 Claim, 23 Drawing Sheets

(51) Int. Cl.
   *A61B 17/00* (2006.01)
   *A61B 18/00* (2006.01)
   *A61B 19/00* (2006.01)

(52) U.S. Cl.
   CPC  *A61B 2017/2927* (2013.01); *A61B 2017/2936* (2013.01); *A61B 2018/0063* (2013.01); *A61B 2018/00601* (2013.01); *A61B 2018/00875* (2013.01); *A61B 2018/1455* (2013.01); *A61B 2019/2211* (2013.01); *A61B 2019/2238* (2013.01)

(56) References Cited

U.S. PATENT DOCUMENTS

| | | |
|---|---|---|
| 3,584,629 A | 6/1971 | Hoef et al. |
| 4,606,343 A | 8/1986 | Conta et al. |
| 5,312,023 A | 5/1994 | Green et al. |
| 5,403,342 A | 4/1995 | Tovey et al. |
| 5,456,401 A | 10/1995 | Green et al. |
| 5,779,130 A | 7/1998 | Alesi et al. |
| 5,842,993 A | 12/1998 | Eichelberger et al. |
| 6,050,989 A | 4/2000 | Fox et al. |
| 7,137,980 B2 | 11/2006 | Buysse et al. |
| 7,156,846 B2 | 1/2007 | Dycus et al. |
| 7,208,005 B2 | 4/2007 | Frecker et al. |
| 7,255,697 B2 | 8/2007 | Dycus et al. |
| 7,441,684 B2 | 10/2008 | Shelton, IV et al. |
| 8,475,453 B2 | 7/2013 | Marczyk et al. |
| 8,721,640 B2 | 5/2014 | Taylor et al. |
| 8,968,312 B2 | 3/2015 | Marczyk et al. |
| 2002/0096550 A1 | 7/2002 | Green et al. |
| 2005/0165435 A1 | 7/2005 | Johnston et al. |
| 2005/0273084 A1 | 12/2005 | Hinman et al. |
| 2006/0000868 A1 | 1/2006 | Shelton et al. |
| 2006/0111210 A1 | 5/2006 | Hinman |
| 2006/0229665 A1 | 10/2006 | Wales et al. |
| 2007/0125826 A1 | 6/2007 | Shelton |
| 2007/0141529 A1 | 6/2007 | Bouneff |
| 2007/0173814 A1 | 7/2007 | Hixson et al. |
| 2007/0175951 A1 | 8/2007 | Shelton et al. |
| 2007/0270790 A1 | 11/2007 | Smith et al. |
| 2008/0029576 A1 | 2/2008 | Shelton et al. |
| 2008/0077159 A1 | 3/2008 | Madhani et al. |
| 2008/0223903 A1 | 9/2008 | Marczyk |
| 2008/0245842 A1 | 10/2008 | Marczyk |
| 2008/0251568 A1 | 10/2008 | Zemlok et al. |
| 2008/0255607 A1 | 10/2008 | Zemlok |
| 2008/0277449 A1 | 11/2008 | Marczyk |
| 2008/0300580 A1 | 12/2008 | Shelton, IV et al. |
| 2008/0308603 A1 | 12/2008 | Shelton et al. |
| 2008/0312668 A1 | 12/2008 | Grace |
| 2009/0001129 A1 | 1/2009 | Marczyk |
| 2009/0012520 A1 | 1/2009 | Hixson et al. |
| 2009/0054733 A1 | 2/2009 | Marescaux et al. |
| 2009/0088792 A1 | 4/2009 | Hoell, Jr. et al. |
| 2009/0090764 A1 | 4/2009 | Viola |
| 2009/0112229 A1 | 4/2009 | Omori et al. |
| 2009/0138006 A1 | 5/2009 | Bales et al. |
| 2009/0171147 A1 | 7/2009 | Lee et al. |
| 2009/0182327 A1 | 7/2009 | Unger |
| 2009/0209990 A1 | 8/2009 | Yates et al. |
| 2010/0032470 A1 | 2/2010 | Hess et al. |
| 2010/0042140 A1 | 2/2010 | Cunningham |
| 2010/0076433 A1 | 3/2010 | Taylor et al. |
| 2010/0076474 A1 | 3/2010 | Yates et al. |
| 2010/0087818 A1 | 4/2010 | Cunningham |
| 2010/0089972 A1 | 4/2010 | Marczyk |
| 2010/0089974 A1 | 4/2010 | Shelton, IV |
| 2010/0179540 A1 | 7/2010 | Marczyk et al. |
| 2011/0021871 A1 | 1/2011 | Berkelaar |

FOREIGN PATENT DOCUMENTS

| | | |
|---|---|---|
| WO | 95/03001 A1 | 2/1995 |
| WO | 2009/039506 A1 | 3/2009 |

OTHER PUBLICATIONS

Australian Office Action dated Mar. 27, 2015 corresponding to AU 2013251209.

SURGICAL DEVICE WITH POWERED ARTICULATION WRIST ROTATION

CROSS REFERENCE TO RELATED APPLICATION

The present application is a continuation of U.S. patent application Ser. No. 13/668,346, filed Nov. 5, 2012, which claims the benefit of and priority to U.S. Provisional Application Ser. No. 61/560,456, filed on Nov. 16, 2011, the entire contents of which are incorporated herein by reference.

BACKGROUND

The present disclosure relates to surgical devices and more particularly, the present disclosure relates to a powered surgical device having a motorized articulation and rotation system.

TECHNICAL FIELD

Many surgical devices utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed.

Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulae. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss.

In continuing efforts to reduce the trauma of surgery, interest has recently developed in the possibilities of performing procedures to diagnose and surgically treat a medical condition without any incision in the abdominal wall by using a natural orifice (e.g., the mouth or anus) to access the target tissue. Such procedures are sometimes referred to as endoluminal procedures, transluminal procedures, or natural orifice transluminal endoscopic surgery ("NOTES"). Although many such endoluminal procedures are still being developed, they generally utilize a flexible endoscope instrument or flexible catheter to provide access to the tissue target tissue.

Endoluminal procedures have been used to treat conditions within the lumen including for example, treatment of gastroesophageal reflux disease in the esophagus and removal of polyps from the colon. In some instances, physicians have gone beyond the luminal confines of the gastrointestinal tract to perform intra-abdominal procedures. For example, using flexible endoscopic instrumentation, the wall of the stomach can be punctured and an endoscope advanced into the peritoneal cavity to perform various procedures.

Using such endoluminal techniques, diagnostic exploration, liver biopsy, cholecystectomy, splenectomy, and tubal ligation have reportedly been performed in animal models. After the intra-abdominal intervention is completed, the endoscopic instrumentation is retracted into the stomach and the puncture closed. Other natural orifices, such as the anus or vagina, may also allow access to the peritoneal cavity.

As mentioned above, many endoscopic and endoluminal surgical procedures typically require cutting or ligating blood vessels or vascular tissue. However, this ultimately presents a design challenge to instrument manufacturers who must attempt to find ways to make endoscopic instruments that fit through the smaller cannulae. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue utilizing specialized vessel sealing instruments.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure. Moreover, coagulation of large tissue or vessels results in a notoriously weak proximal thrombus having a low burst strength whereas tissue seals have relatively high burst strength and may be effectively severed along the tissue sealing plane.

More particularly, in order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

It has been found that the pressure range for assuring a consistent and effective seal is between about 290 kPa to about 1570 kPa and, desirably, within a working range of 680 kPa to 1275 kPa. Manufacturing an instrument which is capable of providing a closure pressure within this working range has been shown to be effective for sealing arteries, tissues and other vascular bundles.

Various force-actuating assemblies have been developed in the past for providing the appropriate closure forces to effect vessel sealing. For example, commonly-owned U.S. patent application Ser. Nos. 10/460,926 and 11/513,979 disclose two different envisioned actuating assemblies, the contents of both of these applications are hereby incorporated by reference herein.

During use, one noted challenge for surgeons has been the inability to manipulate the end effector assembly of the vessel sealer to grasp tissue in multiple planes, i.e., off-axis, while generating the above-noted required forces to affect a reliable vessel seal. It has therefore become desirable to develop an endoscopic or endoluminal vessel sealing instrument which includes an end effector assembly capable of being manipulated along multiple axes to enable the surgeon to grasp and seal vessels lying along different planes within a surgical cavity.

Two examples of devices for off axis articulation of an end effector are described in commonly assigned U.S. Published Patent Application Nos. 2010/0076433 and 2010/0179540, the contents of both are incorporated by reference.

As described in the '433 application, endoluminal procedures often require accessing tissue deep in tortuous anatomy of a natural lumen using a flexible catheter or endoscope. Conventional vessel sealing devices may not be appropriate for use in some endoluminal procedures because of a rigid shaft that can not easily negotiate the tortuous anatomy of a natural lumen In view of this, the '433 application discloses an endoscopic vessel sealer having a flexible articulating shaft. However, the endoscopic vessel sealer of the '433 application required manual inputs from the physician or surgeon to cause the end effector to articulate and rotate the end effector through the use of rotating knobs formed integrally with the housing. There are disclosed separate knobs for articulation and rotation. While the inclusion of both articulation and rotation allows for nearly complete wrist like articulation of the end effector, this concept required the use of two hands for effective operation; one hand to hold the instrument and one to turn rotational and/or articulation wheels.

Similarly, the '540 application teaches the use of either two or four control wires to effectuate articulation of the end effector in multiple planes. However, the '540 application also required the surgeon to employ both hands for effective operation, Further, while the use of four wires enabled multi-plane movement, the systems employed to synchronize the movement of the articulating portion of the shaft, were manual and relied on the skill of the surgeon.

A one-handed design for an endoscopic surgical device has also been contemplated by the assignee of the instant application. For example, commonly assigned U.S. Published Patent Application No. 2009/0054734, the contents of which are incorporated by reference, there is disclosed a one-handed surgical device enabling the surgeon to articulate the end effector in combination with rotation of the device such that an approximation of wrist-like movement is possible. However, as disclosed in the '734 Publication, to accomplish the articulation of the end effector, a proximal end of the surgical device must itself be moved off axis. As can be readily understood by those of relevant skill in the art, the necessity of such off axis movement on the proximal end of the surgical device can result in interference of the device with other surgical tools which are also competing for the limited space available through a single access port. Accordingly, while one-handed operation is possible, the interference with other tools presents additional difficulties for the surgeon.

It is therefore desirable to develop an endoscopic or endoluminal vessel sealing instrument having a flexible shaft capable of insertion in a flexible endoscope or catheter which can be operated by one hand of the surgeon. It is also desirable to develop such an end effector incorporated into a housing allowing the surgeon to perform all the necessary articulation of the end effector, while employing just a single hand, and without necessitating off-axis movement of a proximal end of the surgical device, thus allowing the surgeon to utilize the other hand for use of other tools without compromising the space available for such tools.

SUMMARY

One aspect of the present disclosure is directed to a surgical instrument for treating tissue. The instrument includes a housing having a shaft extending there from, the shaft includes at least an articulating portion and an end effector. Connected to, and rotatable with, the proximal end of the shaft is a first casing. An internal frame is housed within the first casing. A plurality of posts, are supported by the internal frame and connected on their distal ends to at least one drive wire, and connected on their proximal ends to a threaded shaft. A second casing is connected to the first casing and rotatable therewith, the second casing houses the threaded shafts. A first electric motor drives a first gear, the first gear interfaces with the threaded shafts such that a first pair of the plurality of threaded shaft rotate in the same direction. A second electric motor drives a second gear, said second gear causes the connected shaft and first and second casings to rotate about a common axis. Driving the first gear in a first direction causes said articulating portion to articulate in a first plane.

The surgical instrument may further includes a third electric motor driving a third gear, the third gear driving at least a second pair of the plurality of threaded shafts in the same direction, wherein driving the third gear in a first direction causes the articulation portion to articulate in second plane.

According to another aspect of the present disclosure each pair of threaded shafts includes one left-hand threaded shaft and one right-hand threaded shaft. Further, the first and third gears may interface with planetary gears to drive their respective pairs of threaded shafts, and each threaded shaft may include a spur gear driven by internal gear teeth of said planetary gears.

In another aspect of the present disclosure the surgical instrument includes a control system. The control system may include at least one processor and one memory for storing a control algorithm. Further the first, second, and third motors may include an encoder providing feedback to the control system of the mechanical motion of the motor.

Another aspect of the present disclosure is a user input providing desired end effector movement data to the control system, wherein said control system interprets the input end effector movement data and signals one or more of the first, second, or third motors in accordance with said end effector movement data.

According to a further aspect of the invention the control system may include a control algorithm stored in the memory, for controlling the movement of the end effector in response to the input end effector movement data. In one aspect of the invention, the algorithm and control system synchronize the movements of the first, second, and third motors and enable movement of the end effector and articulating portion in multiple planes simultaneously.

The user input may be selected from the group consisting of a button, a toggle, a joystick, a pressure sensor, a switch, a trackball, a dial, an optical sensor, and any combination thereof.

According to a further aspect of the invention, the surgical instrument includes an electrosurgical energy source, the electrosurgical energy source provides energy to one or more seal plates operably connected to the end effector. The end effector is movable from an open position to a closed position upon actuation of a movable handle, and application of said electrosurgical energy is prevented until the end effector has been moved to the closed position. The surgical instrument may also include a knife for severing tissue following formation of a seal in said tissue by application of said electrosurgical energy.

These and other aspects of the present disclosure are described in greater detail and set forth in the following drawings and detailed description.

BRIEF DESCRIPTION OF THE DRAWINGS

Various embodiments of the subject instrument are described herein with reference to the drawings wherein.

Figure 1:
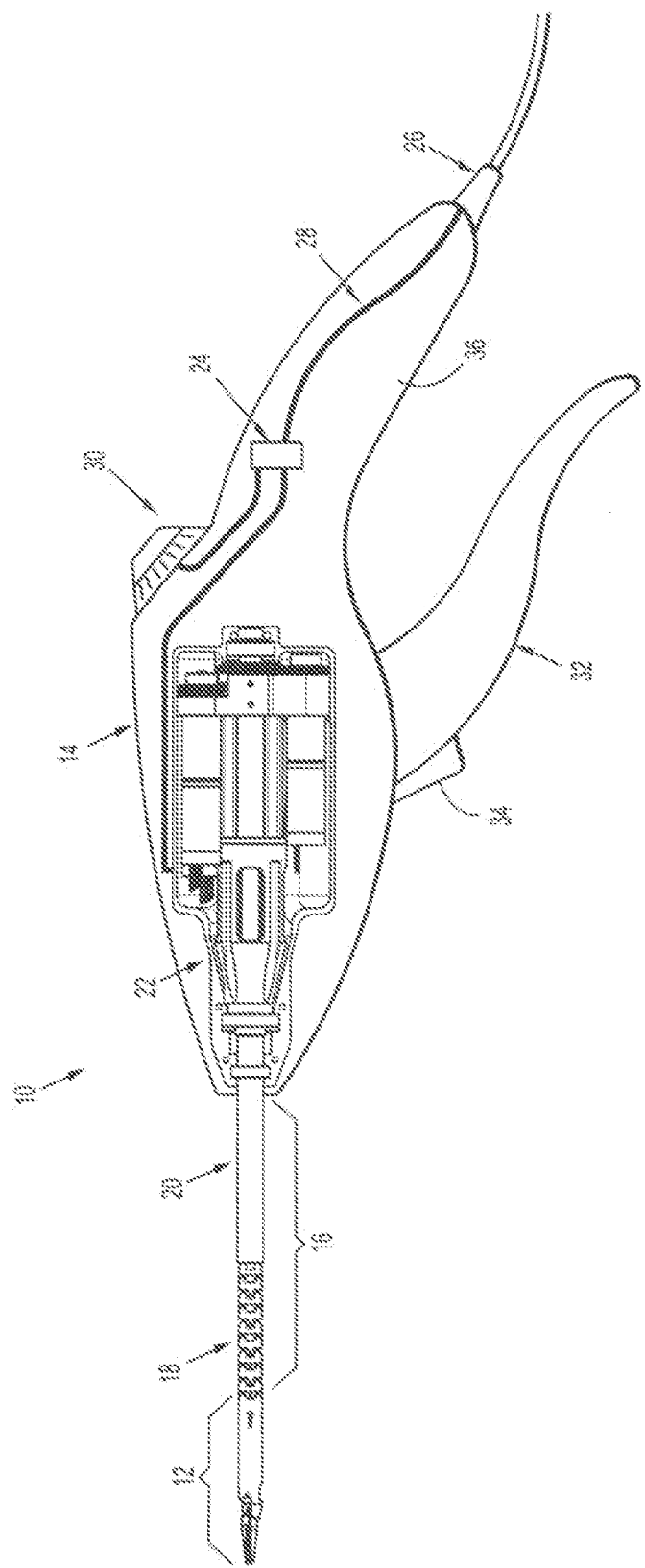
FIG. 1 is a perspective view of an endoscopic forceps showing a housing, a flexible shaft and an end effector assembly according to the present disclosure.

These and other aspects of the present disclosure will be discussed in greater detail below.

DETAILED DESCRIPTION

The present disclosure relates to a powered endoscopic instrument such as an endoscopic forceps utilizing an elongated, generally flexible and articulating shaft. Another aspect of the present disclosure is directed to electrosurgical endoscopic devices and more particularly to endoscopic electrosurgical forceps for sealing and/or cutting tissue utilizing an elongated, generally flexible and articulating shaft. In one embodiment, for example, such a device comprises a handle, handle assembly or other suitable actuating mechanism (e.g., robot, etc.) connected to a proximal end of a flexible, elongated body portion or shaft. A distal portion of the flexible shaft includes an articulating portion comprised of one or more joints to allow articulation of an end effector away from the longitudinal axis in response to actuation of articulation cables. An end effector is operatively supported on a distal end of the flexible shaft. The end effector includes a pair of jaws that can be actuated between a closed position and an open position. The jaws may be adapted to supply electrical energy to tissue grasped between the jaws. The end effector may also include a knife assembly that can be actuated to cut tissue grasped within the jaws.

The functions of opening and closing the jaws; operating the knife assembly; and articulating the end effector can be performed remotely from the handle by actuation of various mechanisms in the handle. Mechanical motion may be transmitted from the handle through the flexible shaft to the end effector by flexible or rigid cables or rods within the flexible shaft. For example, in one embodiment two cables are used to provide articulation; one push-pull style cable opens and closes the jaws; and a second push-pull style cable actuates the knife assembly. One aspect of the device of the present disclosure is adapted to be placed in a lumen of a flexible endoscope and then inserted into a natural orifice of a patient and transited endoluminally through the anatomy of the natural lumen to a treatment site within or outside the natural lumen. Alternatively, the device may be inserted into the body of a patient via a surgical port, or other means known to those of skill in the art. In the drawings and in the descriptions which follow, the term "proximal," as is traditional, will refer to the end of the electrosurgical device and its components which is closer to the user, while the term "distal" will refer to the end which is farther from the user.

FIG. 1 shows the general view of one aspect of the present disclosure. FIG. 1 depicts an endoscopic device 10. The endoscopic device includes an end effector 12 connected to a housing or body 14 via a shaft 16. The shaft 16 is composed of an articulating portion 18, and a non-articulating portion 20. The articulating portion 18 of the shaft 16 may be made of a series of moveable links, and will be discussed in greater detail below. Shaft 16 contains steering cables and activation members like wires, rods, cables etc., for clamping, cutting, or delivering energy to the end effector 12. As noted above shaft 16 connects to body 14, and in particular connects to a steering unit 22. Shaft 16 may be formed of a rigid material such as stainless steel, or alternatively a flexible material such as plastic tubing and may incorporate a tube of braided steel to provide axial (e.g., compression) and rotational strength.

Also housed within the body 14 is a control system 24, which may include a programmable microprocessor. Power is supplied to the endoscopic device 10 from an external source, such as an electrosurgical generator, via cable 26 or alternatively may be derived from local batteries incorporated into the housing 14 (not shown). At least one electrical connection 28 is used to power the control system 24. One of the functions of the control system 24 is to control the steering unit 22, and in particular to control the actuation of steering control motors, which are incorporated in to the steering unit 5, and will be discussed in greater detail below.

As shown in FIG. 1, an activation switch 30 is formed on the top of the body 14 of the endoscopic device 10. The activation switch 30 enables the user or surgeon to input the desired commands to the control system 24, which in turn drives the steering unit to effectuate articulation and/or rotation of the end effector 12. Additional activation elements may also be incorporated such as clamping handle 32 which can control opening and closing of the end effector 12 in order to grasp tissue. A trigger 34 may be provided to effectuate application of electrosurgical energy for sealing or cutting tissue held within the end effector 12. Additionally, or alternatively the trigger 34 may actuate a knife blade, as will be discussed in detail below.

It is contemplated that according to aspects of the present disclosure relating to the use of electrosurgical energy for sealing or cutting tissue the power source supplying power to cable 26 may be a generator such as those sold by Covidien e.g., the LIGASURE™ Vessel Sealing Generator or the Force Triad™ Generator.

The generator may include various safety and performance features including isolated output, independent activation of accessories and/or so-called "Instant Response™" software which is a proprietary technology owned by Covidien. Instant Response™ is an advanced feedback system which senses changes in tissue 200 times per second and adjusts voltage and current to maintain appropriate power. The Instant Response™ technology is believed to provide one or more of the following benefits to vessel sealing: consistent clinical effect through all tissue types; reduced thermal spread and risk of collateral tissue damage; less need to "turn up the generator"; and designed for the minimally invasive environment.

Figure 2:
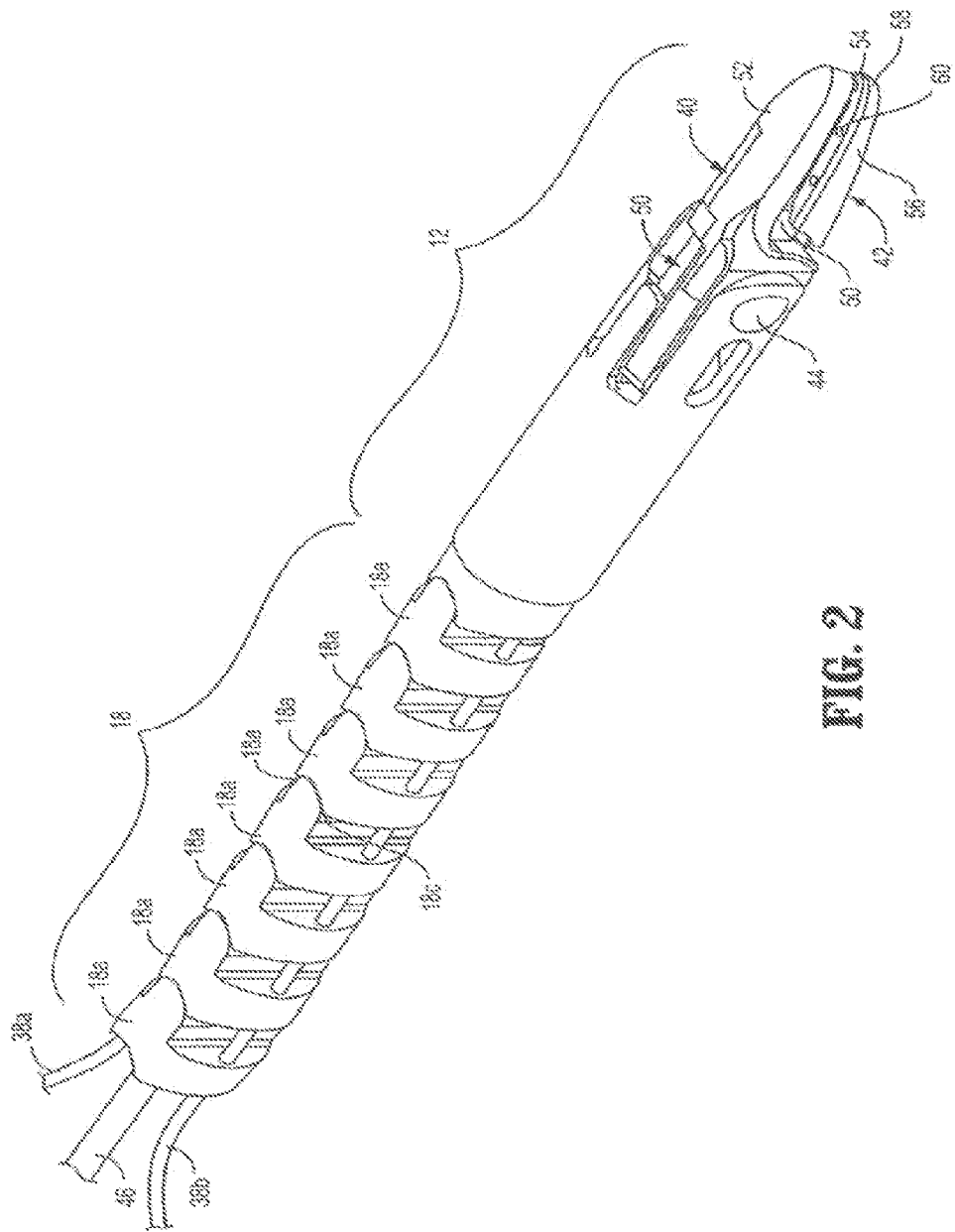
FIG. 2 is an enlarged front, perspective view of the flexible shaft and the end effector assembly of FIG. 1.

Turing now to FIG. 2, there is depicted a close-up view of the end effector 12, and articulated portion 18. The articulated portion 18 is flexible and contains one or more moving joints 18a. A flexible casing or sleeve (not shown) may be employed to protect a plurality of internal moving joints 18a of the articulated portion 18. Articulation of the articulating portion 18, using the moving joints 18a is accomplished by manipulation of articulation cables 38a, 38b.

As mentioned above, end effector 12 is attached at the distal end of the endoscopic device 10 and includes a pair of opposing jaw members 40 and 42. Movable handle 32 is connected to a drive assembly which mechanically cooperates to impart movement of the jaw members 40 and 42 from an open position wherein the jaw members 40 and 42 are disposed in spaced relation relative to one another, to a clamping or closed position, wherein the jaw members 40 and 42 cooperate to grasp tissue there between, as depicted in FIG. 2.

The end effector 12 may be designed as a unilateral assembly, i.e., jaw member 42 is fixed relative to the shaft 16 and jaw member 40 pivots about a pivot pin 44 to grasp tissue or a bilateral assembly, i.e., both jaw members 40 and 42 move relative to a common axis A drive rod 46 or drive sleeve is operably coupled to a drive assembly (not shown) and selectively reciprocable via movement of, for example moveable handle 32 in the direction of fixed handle 36 to actuate, i.e., pivot, the jaw members 40 and 42 relative to one another. In an embodiment of the device, drive rod 46 is flexible, and may be, for example, a cable.

Figure 3:
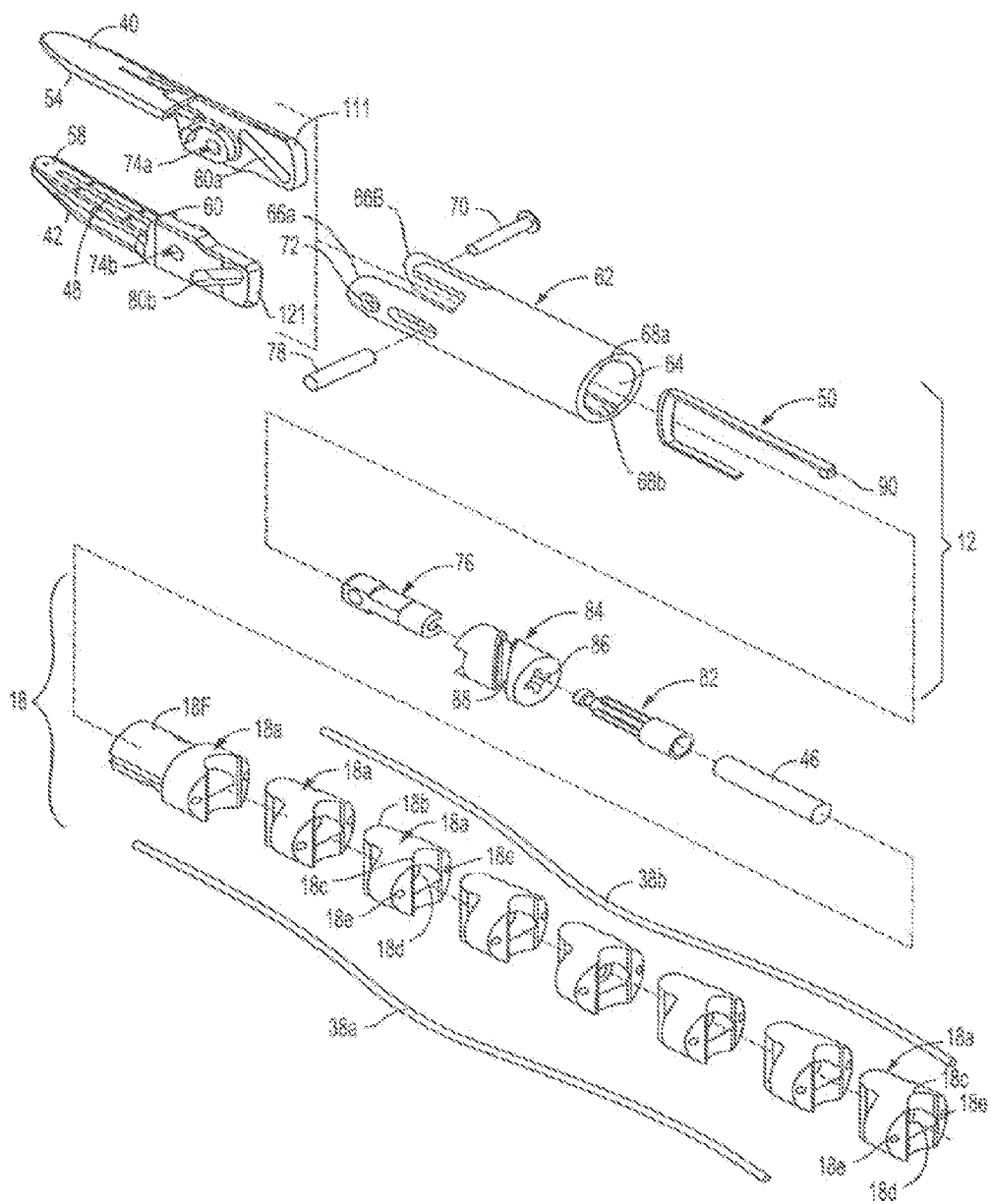
FIG. 3 is an enlarged exploded rear perspective view of the flexible shaft and end effector of FIG. 1.

According to the present disclosure and as best illustrated in FIG. 3, a knife channel 48 may be defined in the upper and/or lower jaw member 40 and 42, respectively (though not shown in the upper jaw in FIG. 3). The knife channel 48 is dimensioned to run through the center of the jaw members 40 and 42, respectively, such that a blade 50 may be selectively reciprocated to cut the tissue grasped between the jaw members 40 and 42 when the jaw members 40 and 42 are in a closed position. Blade 50 may be configured (or the blade 50 in combination with the end effector 12 or drive assembly) such that the blade 50 may only be advanced through tissue when the jaw members 40 and 42 are closed thus preventing accidental or premature activation of the blade 50 through the tissue.

As best shown in FIGS. 2 and 3, jaw member 40 includes an insulative jaw housing 52 and an electrically conductive surface or seal plate 54. Insulator 52 is dimensioned to securely engage the electrically conductive sealing surface 54 by stamping, by overmolding, by overmolding a stamped electrically conductive sealing plate and/or by overmolding a metal injection molded seal plate. All of these manufacturing techniques produce jaw member 40 having an electrically conductive surface 54 which is substantially surrounded by an insulative jaw housing 52. Jaw member 40 may also include one or more wire guides or channels (not shown) which are designed to allow a lead to be in electrical continuity with sealing surface 54.

Jaw member 42 includes similar elements to jaw member 40 such as an insulative jaw housing 56 and an electrically conductive sealing surface or seal plate 58 which is dimensioned to securely engage the insulative jaw housing 56. The electrically conductive surfaces 54, 58 and the insulative jaw housing 52, 56, when assembled, include a longitudinally-oriented channel 48 defined there through for reciprocation of the knife blade 50. As mentioned above, when the jaw members 40 and 42 are closed about tissue, knife channel 48 allows longitudinal extension of the knife 50 in a distal fashion to sever tissue along the tissue seal. A single knife channel, e.g., 48, may be completely disposed in one of the two jaw members, e.g., jaw member 40 or 42, depending upon a particular purpose. Jaw member 42 may be assembled in a similar manner as described above with respect to jaw member 40.

Jaw member 42 includes a series of stop members 60 disposed on the inner facing surfaces of the electrically conductive sealing surface 56 to facilitate gripping and manipulation of tissue and to define a gap "G" between opposing jaw members 40 and 42 during sealing and cutting of tissue. The preferred gap "G" between the conductive sealing surfaces 54 and 58 to effectively and reliably seal tissue is between about 0.001 and about 0.006 inches. Stop members 60 may be employed on one or both jaw members 40 and 42 depending upon a particular purpose or to achieve a desired result. Stop members 60 may be thermally sprayed atop the electrically conductive sealing plate 58 or deposited or affixed in any other known fashion in the art. Moreover, the stop members 60 may be disposed in any configuration along the electrically conductive jaw surfaces 54 and 58 depending upon a particular jaw configuration or desired surgical result.

An electrical lead (not shown) carries a first electrical potential to jaw member 40 and a second electrical potential is transferred through drive rod 46 (or, alternatively, the above mentioned sleeve) to jaw member 42. Upon activation, the two electrical potentials transmit electrical energy through tissue held between conductive seal plates 54 and 58.

Proximal movement of the drive rod 46 pivots the jaw members 40 and 42 to a closed position. More particularly, to once actuated, handle 32 moves in a generally arcuate fashion towards fixed handle 36 which causes reciprocating drive rod 142 to move in a generally proximal direction to close the jaw members 40 and 42. In one embodiment proximal rotation of the handle 32 causes a locking flange associated with trigger 34 to release, i.e., "unlock", allowing for selective actuation of the knife 50. Once the tissue is grasped (within the required pressure range of about 290 kPa to about 1570 kPa), the user then selectively applies electrosurgical energy to effectively seal tissue. Once sealed, the user then selectively advances the knife 50 by actuating the trigger 34 to cut the tissue along the tissue seal. In one embodiment, for example, actuation of the trigger assembly 34 causes a cable extending through shaft 16 and operatively coupled to knife 50 to move distally to thereby cut tissue along the tissue seal. In another embodiment, trigger assembly includes gearing that translates actuation of the trigger assembly to rotational motion of a cable extending through shaft 16.

As described above, with respect to FIGS. 2 and 3, the electrosurgical device includes a plurality of joints 18a which are nestingly arranged in series to form flexible articulating portion 18. The distal end of articulating portion 18 mechanically engages the end effector 12 and the proximal end mechanically engages the shaft 20. Each of the plurality of joints 18a of the flexible shaft 18 includes a distal knuckle 18b and a proximal clevis 18c formed therewith. Each knuckle 18b operatively engages a clevis 18c of an adjacent joint 18a. Each joint 18a defines a central lumen 18d formed therein and a pair of opposed lumens 18e formed on either side of central lumen 18d. Articulation cables 38a and 38b slideably extend through respective lumens 18e of joints 18a. The operation of cables 38a and 38b is explained in further detail below with respect to FIGS. 7 and 8.

As seen in FIG. 3, end effector 12 includes a jaw support member 62 which is configured to pivotably support jaw members 40 and 42. Jaw support member 62 defines a lumen 64 in a proximal end thereof and a pair of spaced apart arms 66a and 66b in a distal end thereof. Lumen 64 is configured and dimensioned to receive a stem 18f extending from a distal-most joint 18a of articulating portion 18 of shaft 16. Lumen 64 includes a pair of opposed channels 68a, 68b in a surface thereof which are configured to slidingly receive the knife blade 50 for reciprocation therein.

Jaws 40 and 42 are pivotably mounted on support member 62 by a jaw pivot pin 70 which extends through apertures 72 formed in arms 66a and 66b of support member 62 and respective apertures 74a, 74b formed in jaw members 40 and 42. To move jaws 40 and 42 between an open position and a closed position, an axially or longitudinally movable center rod 76 having a camming pin 78 is mounted within jaw support 62 at the distal end of center rod 76. Camming pin 78 rides in and engages angled camming slots 80a and 80b formed in respective jaw members 40 and 42 such that axial or longitudinal movement of the center rod 76 via drive rod 46 causes jaws 40 and 42 to cam between open and closed positions.

End effector 12 includes a keyed rod 82 having a distal end rotatably connected to a proximal end of center rod 76. Keyed rod 82 includes a proximal end fixedly connected to a distal end of drive rod 46, and a body portion, disposed between distal end and proximal end, having a non-circular cross-sectional profile.

End effector 12 further includes a camming hub 84 having a lumen 86 defined therethrough configured and adapted to slideably receive the body portion of keyed rod 82 therein. Camming hub 84 includes a mating mechanical interface defined therein which cooperates with the outer peripheral configuration of body portion of keyed rod 82 to allow positive engagement of the two component halves for rotational purposes as explained in more detail below. The camming hub 84 also includes a helical or spiral groove 88 defined in an outer surface thereof which is configured to mechanically engage a detent protrusion 90 of the knife 50 the purpose of which is also explained in more detail below. Camming hub 84 is configured for rotatable disposition within lumen 64 of support member 62. In an alternative embodiment, camming hub 84 may be replaced by other mechanisms to translate rotational motion to linear motion (e.g., a lead screw, one or more gears, and the like).

In operation, the drive rod 46 is configured to provide two distinct and separate functions: axial displacement thereof actuates the jaw members 40 and 42 between the open to closed positions and rotational movement thereof advances the knife 50 through tissue. More particularly, axial displacement of drive rod 46 imparts axial displacement to keyed rod 82 which, in turn, imparts axial displacement to center rod 76. However, since camming hub 84 slidably supports keyed rod 82, no axial displacement is imparted thereto, and keyed rod 82 is able to slidingly traverse the camming hub 84 to impart axial force on the center rod 76.

Figure 4:
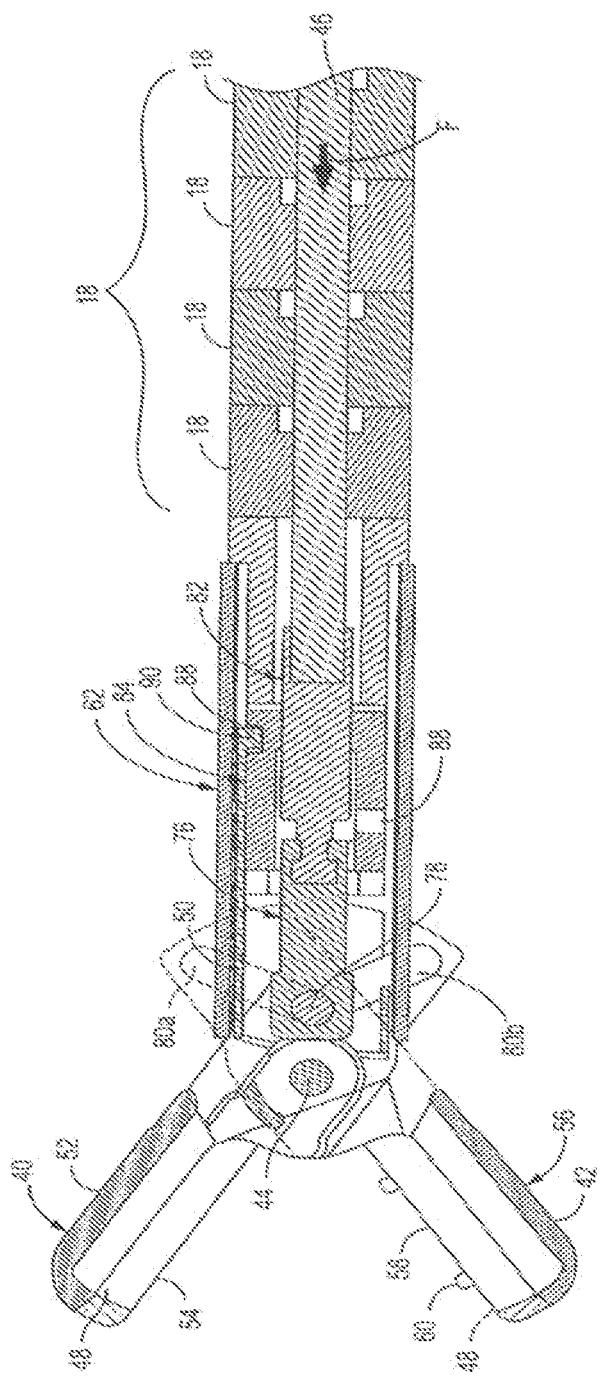
FIG. 4 is a side cross section of the flexible shaft and end effector assembly of FIG. 2 shown in an open configuration.
Figure 5:
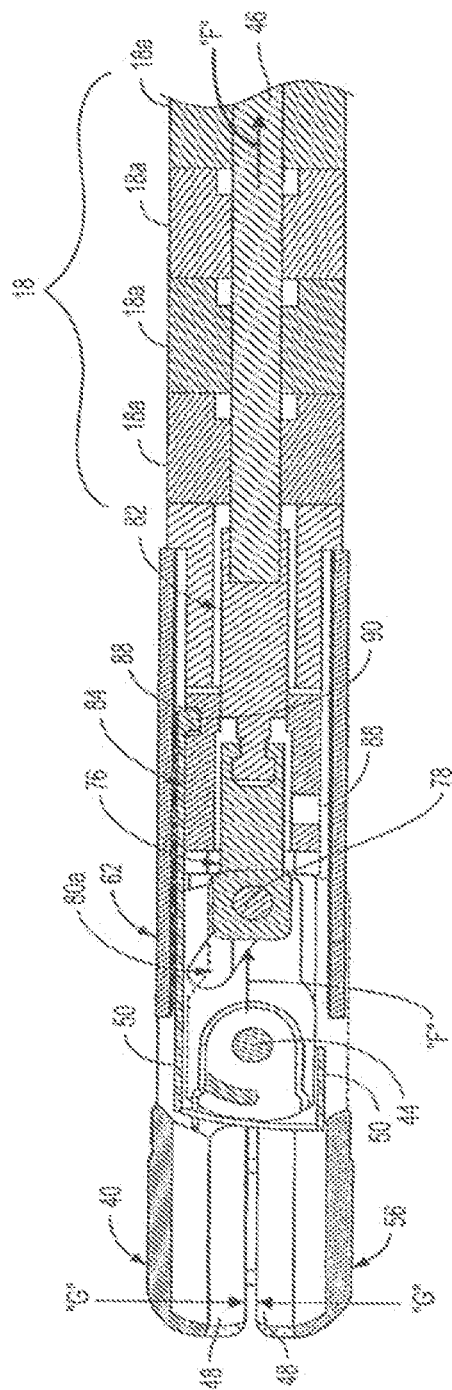
FIG. 5 is a side cross section of the flexible shaft and end effector assembly of FIG. 2 shown in a closed configuration.

As best shown in the progression from FIG. 4 to FIG. 5, proximal translation of the drive rod 46 in the direction of arrow "F" forces camming pin 78 proximally within camming slots 80a and 80b to close the jaw members 40 and 42 about tissue with the requisite closure pressure and within the requisite gap "G" range. In an alternative embodiment (not shown), the functions actuated by drive rod 46 may be reversed with axial displacement advancing the knife 50 and rotational motion opening and closing jaw members 40 and 42. The electrically conductive sealing plates 54, 58 are then energized to transmit electrical energy through tissue held between the jaw members 40 and 42.

Once a proper tissue seal is formed, the tissue may be severed along the tissue seal. Again, one or more safety features may be employed to assure that a proper seal has been formed prior to severing tissue. For example, the generator may include a safety lockout which electrically prevents or electro-mechanically prevents actuation of the knife 50 unless a proper and effective seal has been formed. As mentioned above, it is also important to note that vessel or tissue sealing is more than simply coagulating tissue and requires precise control of pressure, energy and gap "G" to effectively seal tissue.

As noted above the present disclosure incorporates a knife 50 which, when activated via the trigger 34, progressively and selectively divides the tissue along an ideal tissue plane in precise manner to effectively and reliably divide the tissue into two sealed halves. The knife 50 allows the user to quickly separate the tissue immediately after sealing without substituting a cutting instrument through a cannula or trocar port.

It is envisioned that knife blade 50 may also be coupled to the same or an alternative electrosurgical energy source to facilitate separation of the tissue along the tissue seal. Moreover, it is envisioned that the angle of the blade tip of knife blade 50 may be dimensioned to provide more or less aggressive cutting angles depending upon a particular purpose. For example, the knife blade 50 may be positioned at an angle which reduces "tissue wisps" associated with cutting. Moreover, the knife blade 50 may be designed having different blade geometries such as serrated, notched, perforated, hollow, concave, convex etc. depending upon a particular purpose or to achieve a particular result. It is envisioned that the knife 50 generally cuts in a progressive, uni-directional fashion (i.e., upon distal movement). As mentioned above, the drive rod performs two functions, opening and closing the jaw members 40 and 42 and advancing the knife 50 to sever tissue. In order to sever the tissue, rotation of drive rod 46 imparts rotation to keyed rod 82 which, in turn, imparts rotation to camming hub 84. The distal end of the keyed rod 82 is allowed to rotate within the proximal portion of center rod 76. Thus center rod 76, which is connected at its distal end to camming pin 78 does not rotate.

End effector 12 is operably coupled to a knife 50 which is slidably supported within respective channels 68a and 68b of support member 62. More particularly, knife 50 includes a sharpened or serrated edge at a distal end thereof and a pair of guide flanges proximally there from. The proximal end of knife blade 50 includes a protrusion 90 which is configured to engage and ride within spiral or helical groove 88 defined in camming hub 84.

Figure 6:
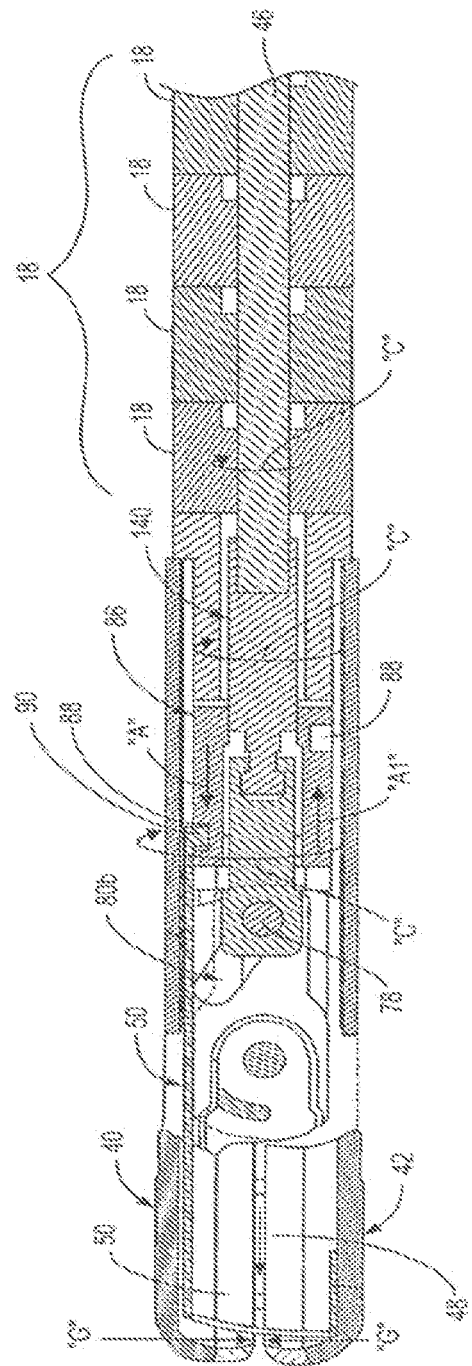
FIG. 6 is a side cross section of the flexible shaft and end effector of FIG. 2 showing distal translational movement of a cutting mechanism configured to cut tissue disposed within jaw members of the end effector assembly.

In operation, as shown in FIG. 6, as camming hub 84 is rotated in direction of arrow "C", proximal end 90 rides within groove 88 of camming hub 84 and moves in an axial direction "A" relative thereto. Rotation of the camming hub 84 in one direction forces the blade 50 distally through knife channels 48 in jaw member 40 and/or 42 to sever tissue disposed there between. Rotation in the opposite direction forces proximal end 90 proximally to retract blade 50 to a proximal-most position. A spring may be operatively associated with the camming hub 84 to bias the knife 50 in a proximal-most orientation.

Figure 7:
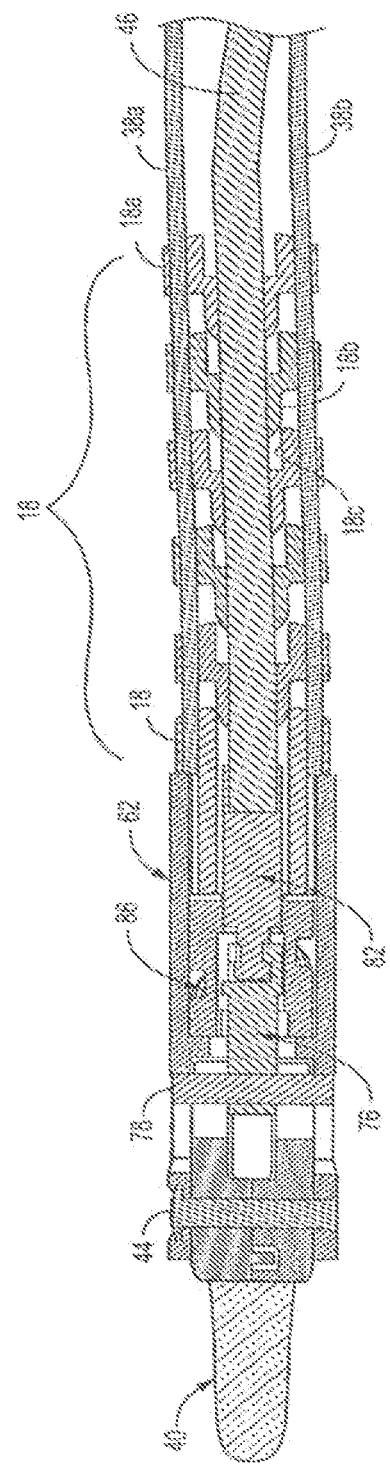
FIG. 7 is a longitudinal, cross-sectional view of the end effector assembly of FIG. 2 in an un-articulated condition.

As mentioned above, the end effector 12 may be selectively articulated. More particularly, as seen in FIG. 7 with end effector 12 in an axially aligned condition, in order to articulate end effector assembly 12 at least one articulation cable (38a, 38b) operable from the body 14 is employed. Each articulation cable (38a, 38b) includes a distal end operatively connectable with an end effector 12 and a proximal end operatively connected to at least one control element, such as, for example a drive motor, as will be described in greater detail below. In one example using two articulation cables 38a, 38b, movement of the control element results in movement of the a first articulation cable 38a, wherein movement of the first articulation cable 38a in a first direction causes an articulation of the end effector 12 in a first direction. Similarly, movement of the second articulation cable 38b in a second direction results in articulation of the end effector 12 in a second direction. This is generally referred to herein as a two-wire articulation system and method.

Figure 8:
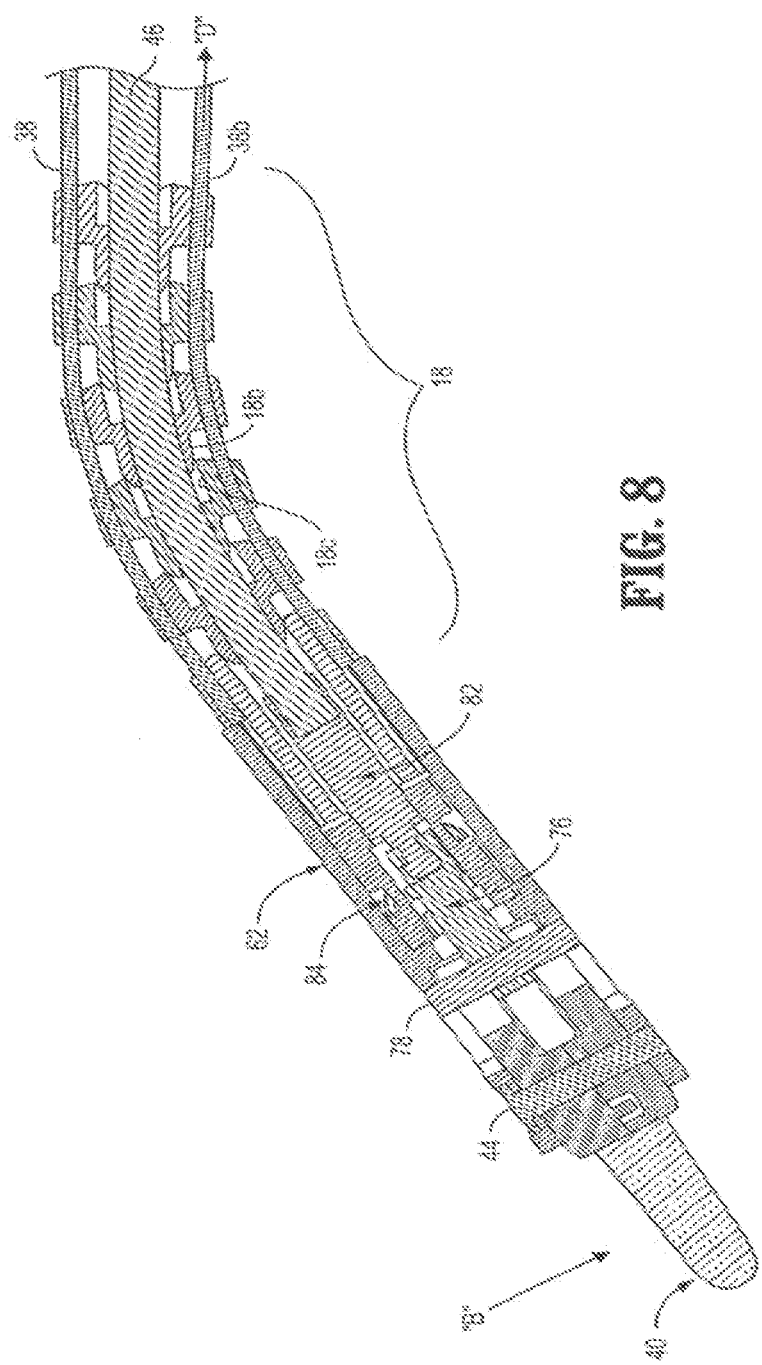
FIG. 8 is a longitudinal, cross-sectional view of the end effector assembly of FIG. 2 in an articulated condition.
Figure 9:
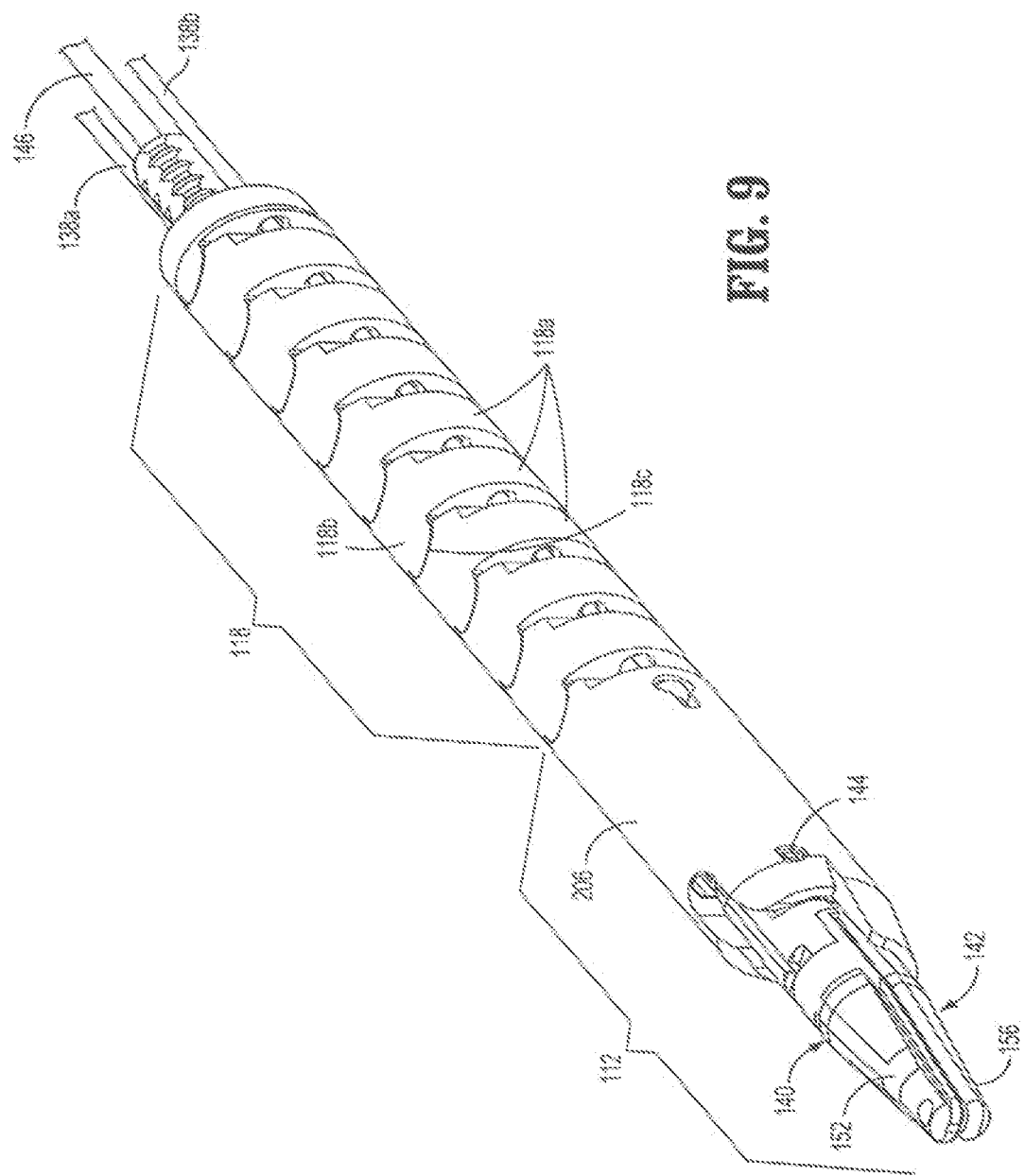
FIG. 9 is an enlarged perspective view of another partially flexible shaft and end effector assembly according to the present disclosure.

More particularly and with reference to FIGS. 7 and 8, when first articulation 38b cable (i.e., the lower articulation cable as depicted in FIGS. 7 and 8) is withdrawn in a proximal direction, as indicated by arrow "D" of FIG. 8, a distal end of articulation cable 38b, anchored to a distal-most joint 18a of articulating portion 18, causes the joints 18a to rotate about the interface between knuckles 18b and clevis' 18c thereby causing gaps defined there between, along a side surface thereof, to constrict. In so doing, end effector 12 is articulated in a downward direction, in the direction of arrow "B", i.e., in a direction transverse to longitudinal axis. In order to return end effector assembly 12 to an un-articulated condition or to articulate end effector assembly 12 in an opposite direction, articulation cable 38a (i.e., the upper articulation cable as depicted in FIGS. 7 and 8) must be withdrawn in a proximal direction and the force applied to articulation cable 38b must be released allowing it to move in the opposite direction.

Various handles and/or handle assemblies may be operatively connected or otherwise associated with end effector 12 in order to effect operation and movement of the various components thereof, i.e., drive cable 46 and/or articulation cables 38a, 38b.

In one envisioned embodiment, the knife 50 may not be included with the endoscopic device 10 and the device may be designed solely for sealing vessels or other tissue bundles.

An alternative two wire end effector assembly and drive mechanism is shown in FIGS. 9-13. Many of the aforedescribed features of end effector 12 and articulation portion 18 described above are similar to that of end effector 112 and articulation portion 118 and for the purposes of consistency, these features are hereby incorporated in the following discussion which is presented below in a more abbreviated form.

End effector 112 includes opposing jaw members 140 and 142 which cooperate to effectively grasp tissue for sealing purposes. The end effector 112 is designed as a unilateral assembly, i.e., jaw member 142 is fixed relative to the articulation portion 118 and jaw member 140 pivots about a pivot pin 144 to grasp tissue.

Figure 10:
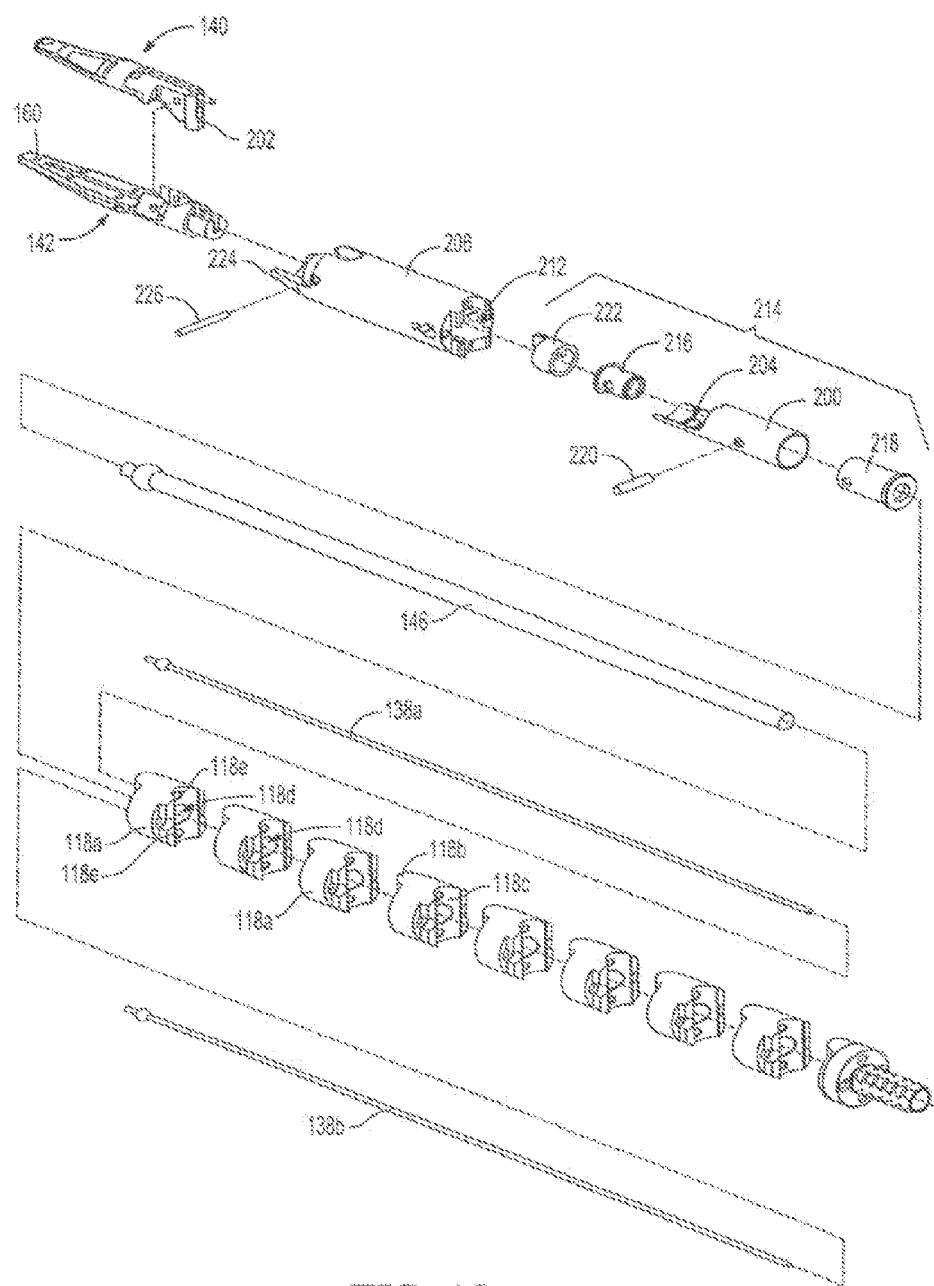
FIG. 10 is an enlarged, exploded perspective view of the partially flexible shaft of FIG. 9.
Figure 11:
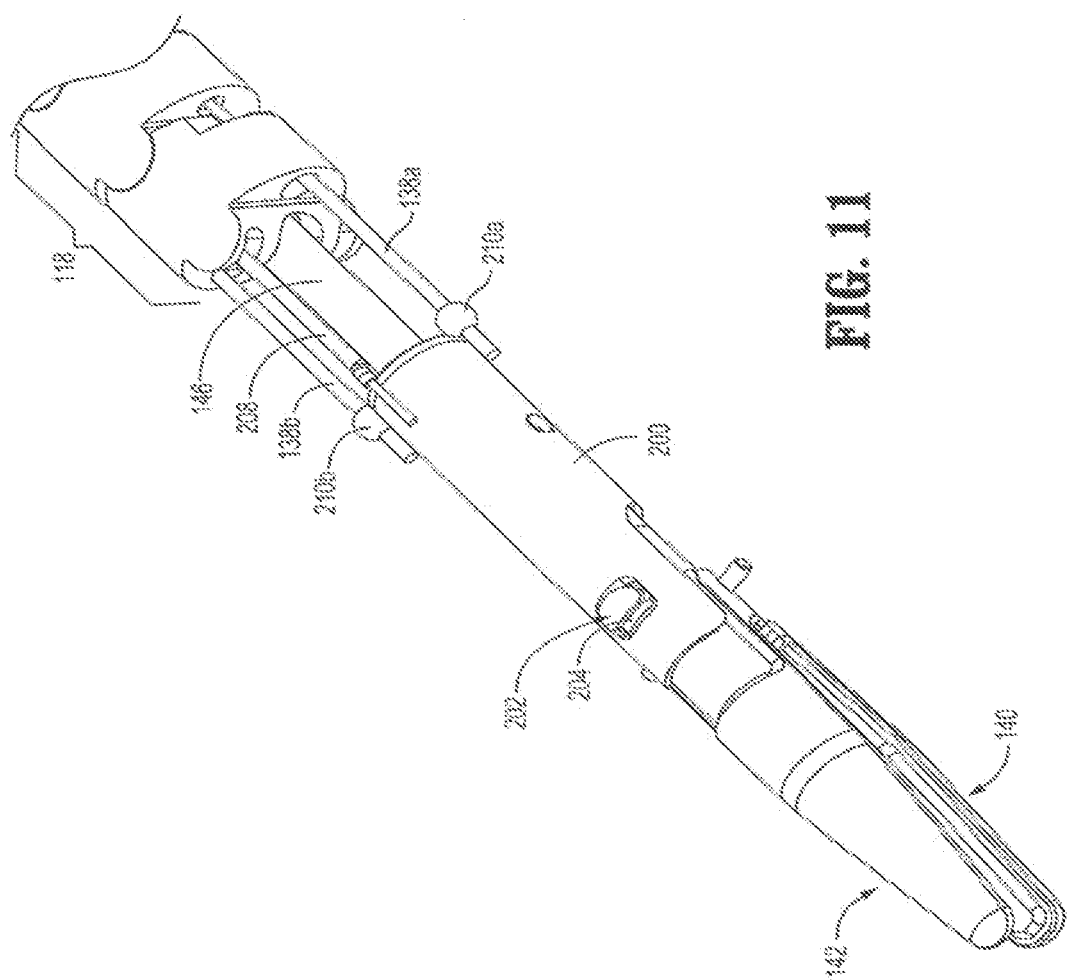
FIG. 11 is a bottom perspective of the partially flexible shaft of FIG. 10 with end effector assembly shown in partially open configuration.
Figure 12:
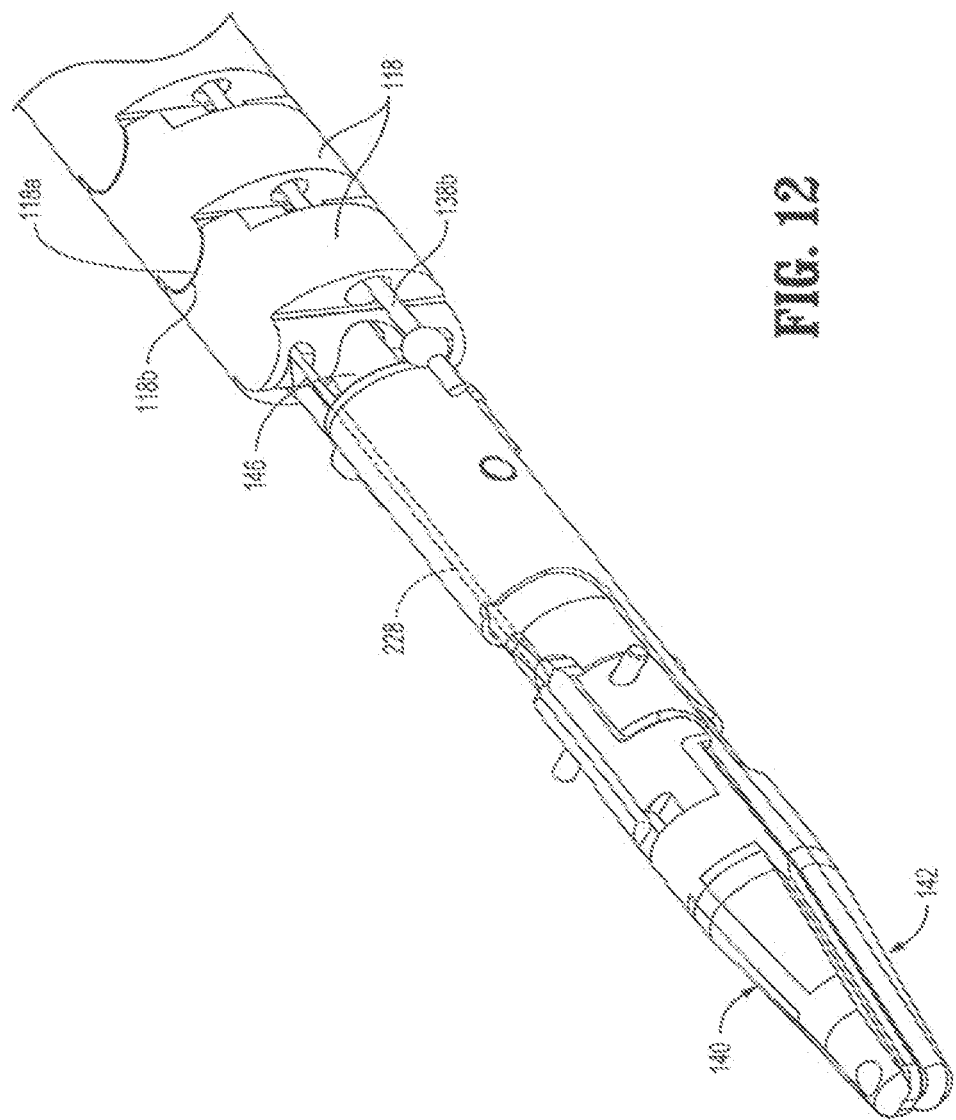
FIG. 12 is a front perspective of the partially flexible shaft of FIG. 10 with end effector assembly shown in closed configuration.

As shown in FIG. 10, a reciprocating sleeve 200 is slidingly disposed within the articulating portion 118 and is remotely operable by the drive assembly (not shown). The pivoting jaw member 140 includes a protrusion 202 which extends from jaw member 140 through an aperture 204 disposed within the reciprocating sleeve 200 (FIGS. 10, 11). The pivoting jaw member 140 is actuated upon by sliding sleeve 200 axially within the coupling portion 206 such that a distal end of the aperture 204 abuts against the protrusion 202 on the pivoting jaw member 140 (See FIG. 11). Pulling the sleeve 200 proximally closes the jaw members 140 and 142 about tissue grasped there between and pushing the sleeve 200 distally opens the jaw members 140 and 142 relative to one another for grasping purposes.

End effector 112 may be structured such that electrical energy can be routed through the sleeve 200 to a protrusion 202 contact point with the sleeve 200 or using a "brush" or lever (not shown) to contact the back of the moving jaw member 140 when the jaw member 140 closes. In this instance, the electrical energy would be routed through the protrusion 202 to one of the jaw members 140 or 142. Alternatively, an electrical lead (not shown) may be routed to energize one of the jaw members, e.g., jaw member 140, and the other electrical potential may be conducted through the sleeve 200 via an electrical contact with lead 208 (See FIG. 11) and transferred to the pivoting jaw member 140 which establishes electrical continuity upon retraction of the sleeve 200.

Jaw members 140 and 142 include similar elements to jaw members 40 and 42 as described above such as jaw insulators 152, 156 and electrically conductive sealing surfaces or seal plates 154 and 158, respectively. Jaw member 142 also includes a series of stop members 160 disposed on the inner facing surface of electrically conductive sealing surface 158 to facilitate gripping and manipulation of tissue and to define a gap "G" between opposing jaw members 140 and 142 during sealing and/or cutting of tissue. It is envisioned that the series of stop members 160 may be employed on one or both jaw members 140 and 142 in a variety of configurations depending upon a particular purpose or to achieve a desired result of the jaw. The stop members 160 insulate the jaw members 140 and 142 preventing shorting and closing the circuit loop in instances when there is no tissue between the jaws.

The end effector 112 may be articulated from an axially aligned condition to an articulated condition. In order to articulate end effector 112 via an articulation arrangement 118 similar to the articulation arrangement described above, two articulation cables 138a and 138b may be utilized to articulate the articulating portion 118. As best seen in FIG. 11, each articulation cable 138a and 138b includes a distal end 210a and 210b which operatively connects with an end effector 112 coupling assembly 206 disposed at the distal end of articulating portion 118. Coupling assembly 206 includes a cavity 212 defined therein configured to receive a series of mechanically inter-cooperating elements 214 which are engaged by drive rod 146 for reciprocation therein as well as guide the various electrical connections to the jaw members 140 and 146. The drive rod 146 is preferably made from a flexible, friction-reducing material to allow the drive rod 146 to bend in a given direction when the articulating portion 118 of shaft 120 is articulated. The friction-reducing material reduces buckling during articulation.

Coupling assembly 206 includes a pair of bushings 216 and 218 which engage and secure a distal end of the drive rod 146 to the drive sleeve 200 via pin 220. Bushing 216 is configured to engage bushing 218 and secure the distal end of drive rod 146 there between. Pin 220 couples the secured bushings 216 and 218 and drive rod 146 to drive sleeve 200. The drive sleeve 200 (and secured drive rod 146) is received within cavity 212 for sliding translation therein upon actuation of the drive assembly (not shown).

Coupling assembly 206 also includes a locking element 222 which is configured to engage a proximal end of jaw member 142 to lock the coupling assembly 206 (and drive rod 146) in fixed relation relative to jaw member 140 to limit any rotational movement there between. Longitudinal translation of the drive rod 146 in the distal direction causes drive sleeve 200 to move longitudinally within the coupling assembly 206 and effectuate opening and closing of the jaw member 140, as described above. The coupling assembly 206 also includes a distal flange 224 which supports the lower jaw member 142 once assembled to connected both jaw members 140, 142 to the coupling assembly 206 via pin 226. As best shown in FIG. 11, the coupling assembly 206 also supports the electrical connection between lead 208 and driving sleeve 200. In addition, coupling assembly 206 also guides electrical lead 228 (shown in phantom in FIG. 12) therethrough for connection to jaw member 140. As detailed above, according to one embodiment of the disclosure one of the leads 208 and 228 may act as the active electrode, and the other act as the return electrode in a typical RF energy system.

Figure 13:
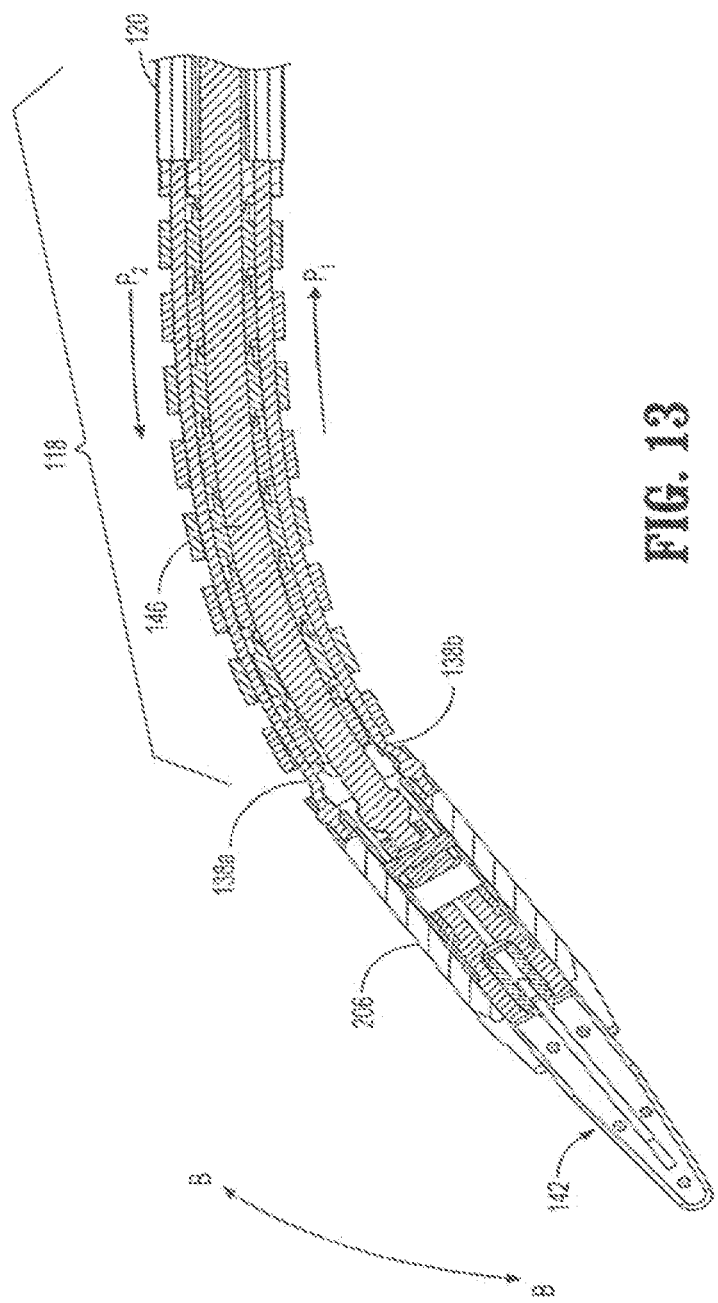
FIG. 13 is a top cross section of the partially flexible shaft of FIG. 10 in an articulated orientation.

In operation, to articulate the articulation portion 118, as best shown in FIG. 13 when one cable 138a is being pulled in the direction of P1, the other cable 138b is being pushed (or relaxed) in the direction of P2 to allow the articulation portion 118 to articulate in a given direction. Similar to FIGS. 2 and 3 above, the articulating portion 118 includes a plurality of joints 118a which are nestingly arranged in series. The distal end either directly or via coupling assembly 206 mechanically engages the end effector 112 and the proximal end engages a shaft 120 (similar to the arrangement discussed above with respect to FIGS. 1-8). Each of the plurality of joints 118a of the articulating portion 118 includes a distal knuckle 118b and a proximal clevis 118c formed therewith. Each knuckle 118b operatively engages a clevis 118c of an adjacent joint 118a. Each joint 118a has a central lumen 118d defined therein and a pair of opposed lumens 118e formed on either side of central lumen 118d. The articulation cables 138a and 138b slideably extend through respective lumens 118e of joints 118a. The articulation cables 138a and 138b are preferably made from a flexible, friction-reducing material.

It is envisioned that a safety mechanism or circuit (not shown) may be employed such that the jaw members 140 and 142 cannot be energized unless they are closed and/or unless the jaw members 140 and 142 have tissue held there between. In the latter instance, a sensor (not shown) may be employed to determine if tissue is held there between. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. U.S. patent application Ser. No. 10/427,832 describes one such feedback system, the entire contents of which being incorporated by reference herein.

From the foregoing and with reference to the various figure drawings, those skilled in the art will appreciate that certain modifications can also be made to the present disclosure without departing from the scope of the same. For example, it is contemplated that the electrosurgical device (and/or the electrosurgical generator used in connection therewith) may include a sensor or feedback mechanism (not shown) which automatically selects the appropriate amount of electrosurgical energy to effectively seal the particularly-sized tissue grasped between the jaw members 140 and 142. The sensor or feedback mechanism may also measure the impedance across the tissue during sealing and provide an indicator (visual and/or audible) that an effective seal has been created between the jaw members 140 and 142. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

In embodiment relating to both end effector 12 and 112, the electrically conductive sealing surfaces 54, 154 and 58, 158 of the jaw members 40, 42 and 140, 142, respectively, are relatively flat to avoid current concentrations at sharp edges and to avoid arcing between high points. In addition and due to the reaction force of the tissue when engaged, jaw members 40, 42 and 140, 142 can be manufactured to resist bending. For example, the jaw members 40, 42 and 140, 142 may be tapered along the width thereof which resists bending due to the reaction force of the tissue. In fact, in some circumstances tapering promotes visualization and allows a greater bend radius than a jaw with a constant cross-section.

It is envisioned that the outer surface of the end effectors 12, 112 may include a nickel-based material, coating, stamping, metal injection molding which is designed to reduce adhesion between the jaw members 40, 42 and 140, 142 with the surrounding tissue during activation and sealing. Moreover, it is also contemplated that the conductive surfaces 54, 58 and 154, 158 of the jaw members 40, 42 and 140, 142, respectively, may be manufactured from one (or a combination of one or more) of the following materials: nickel-chrome, chromium nitride, MedCoat 2000 manufactured by The Electrolizing Corporation of OHIO, inconel 600 and tin-nickel. The tissue conductive surfaces 54, 58 and 154, 158 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 54, 58 and 154, 158 made from or coated with Ni200, Ni201 (~100% Ni) also showed improved non-stick performance over typical bipolar stainless steel electrodes.

Endoscopic device 10, including end effectors 12 and 112 (either with or without articulating portions 18, 118, and shaft 3, 103) may be designed such that they are fully or partially disposable depending upon a particular purpose or to achieve a particular result. For example, end effector 12, 112 may be selectively and releasably engageable with the distal end of the articulation portion 18, 118 and/or the proximal end of shaft 3, 103 may be selectively and releasably engageable with the housing 14 of the endoscopic device 10. In either of these two instances, the endoscopic devices 10 would be considered "partially disposable" or "reposable", i.e., a new or different end effector assembly 12, 112 selectively replaces the old end effector assembly 12, 112 as needed. As can be appreciated, the presently disclosed electrical connections would have to be altered to modify the instrument to a reposable design.

As noted above, other methods of controlling an articulating portion 18, 118 of an electro surgical device are known and described in commonly assigned U.S. Published Patent Application Nos. 2009/0054734 and 2010/0179540, the contents of which are incorporated herein by reference. These control systems, in contrast to those described in detail above, incorporate what is referred to herein as a four-wire system. As a result of using four wires, these systems are able more closely approximate true wrist articulation. Devices employing such systems are able to not only articulate the end effector in a single plane, and then rotate the entire shaft, but to actually articulate the end effector in multiple (e.g. up and down and side to side and any combination thereof). When used in combination with the ability to rotate the end effector, such they are able to closely mimic the degrees of freedom seen in the human wrist.

As these four-wire control systems employ very similar features as the two wire control systems described above, to the extent possible similar number will be used to describe control and articulation of an endoscopic device 10.

Figure 14:
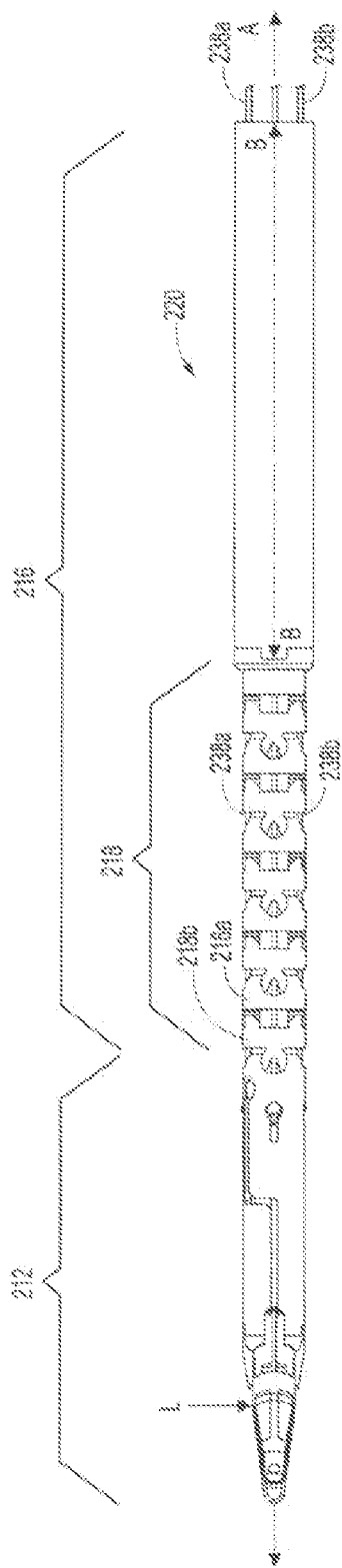
FIG. 14 is an enlarged front, top view of the flexible shaft and the end effector assembly in an un-articulated condition according to another aspect of the present disclosure.

FIG. 14 depicts a perspective view of a shaft 216 and end effector 212. The shaft 216 includes an articulating portion 218 and a non-articulating portion 220. As above the non-articulating portion 220 may exhibit various constructions. For example, the non-articulating portion 220 may be formed from a substantially rigid tube, from flexible tubing (e.g., plastic), or the non-articulating portion 220 may be formed as a composite of a flexible tube and a rigidizing element, such as a tube of braided steel, to provide axial (e.g., compression) and rotational strength. In other embodiments, the non-articulating portion 220 may be constructed from a plastically deformable material. In some embodiments the non-articulating portion 220 exhibits a flexural rigidity that is sufficiently low to permit a surgeon to pre-shape or reshape the non-articulating portion 320 prior to or during a surgical procedure to accommodate the contours and characteristics of the surgical site. Once shaped, the non-articulating portion 220 may define a non-aligned configuration wherein the longitudinal axis of the non-articulating portion 220 is not aligned with the longitudinal axis of the articulating portion 218. The non-articulating portion 220 may also exhibit an axial rigidity that is sufficient to maintain the shape and orientation of the non-aligned configuration during normal surgical use of the endoscopic instrument 10.

Figure 15:
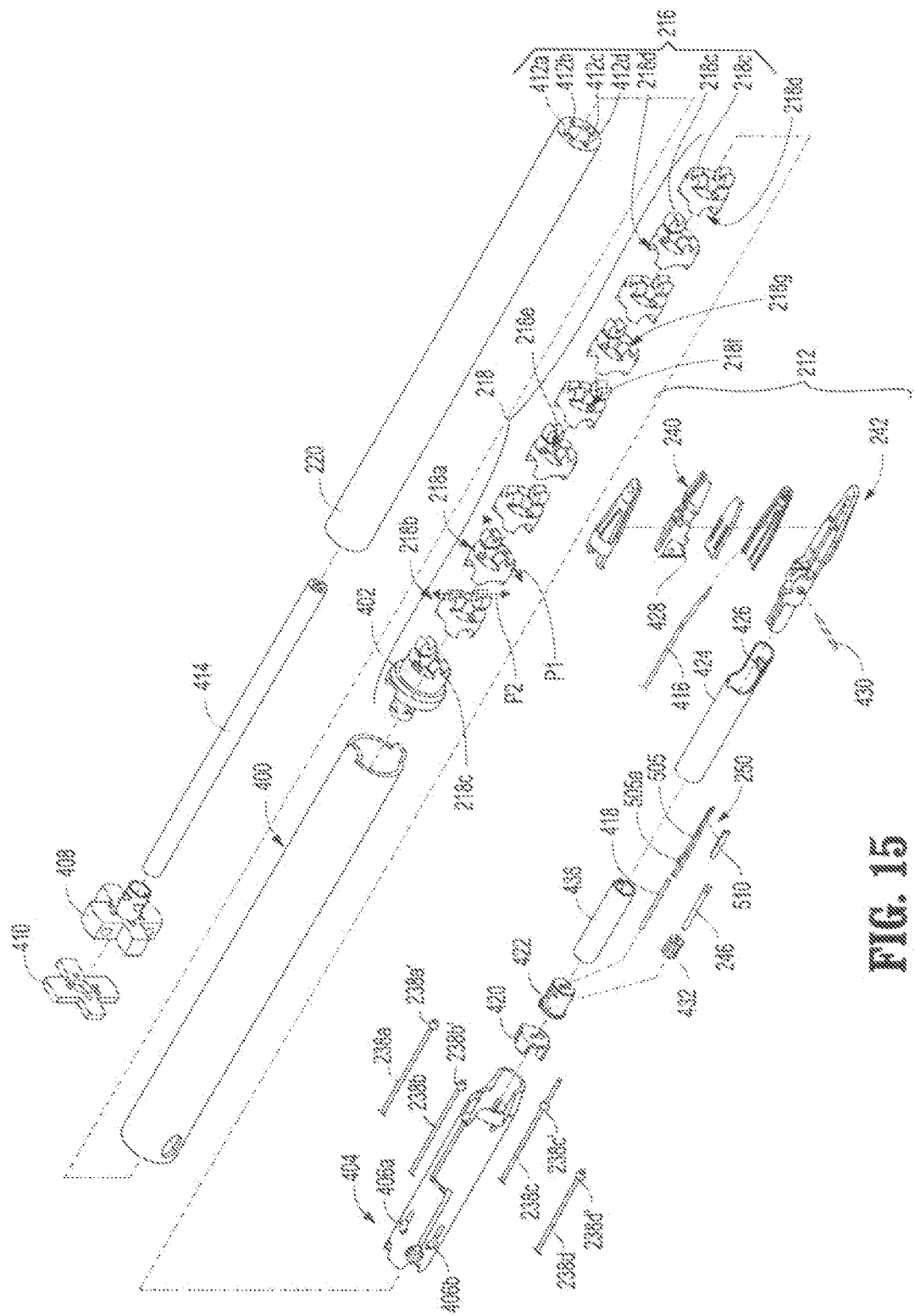
FIG. 15 is an enlarged exploded front perspective view of the flexible shaft and end effector of FIG. 14.

As shown in FIG. 15 the articulating portion 218 of shaft 216 may include an exterior casing or insulating material 400 disposed over a plurality of links 218a, 218b. The links 218a and 218b are configured to pivot relative to one another to permit the articulating portion 218 of the shaft 216 to articulate relative to its longitudinal axis. In one embodiment, the links 218a and 218b are nestingly engaged with one another to permit pivotal motion of the articulating portion 218 in two orthogonal planes in response to movement of an articulation control system, not shown.

Figure 16:
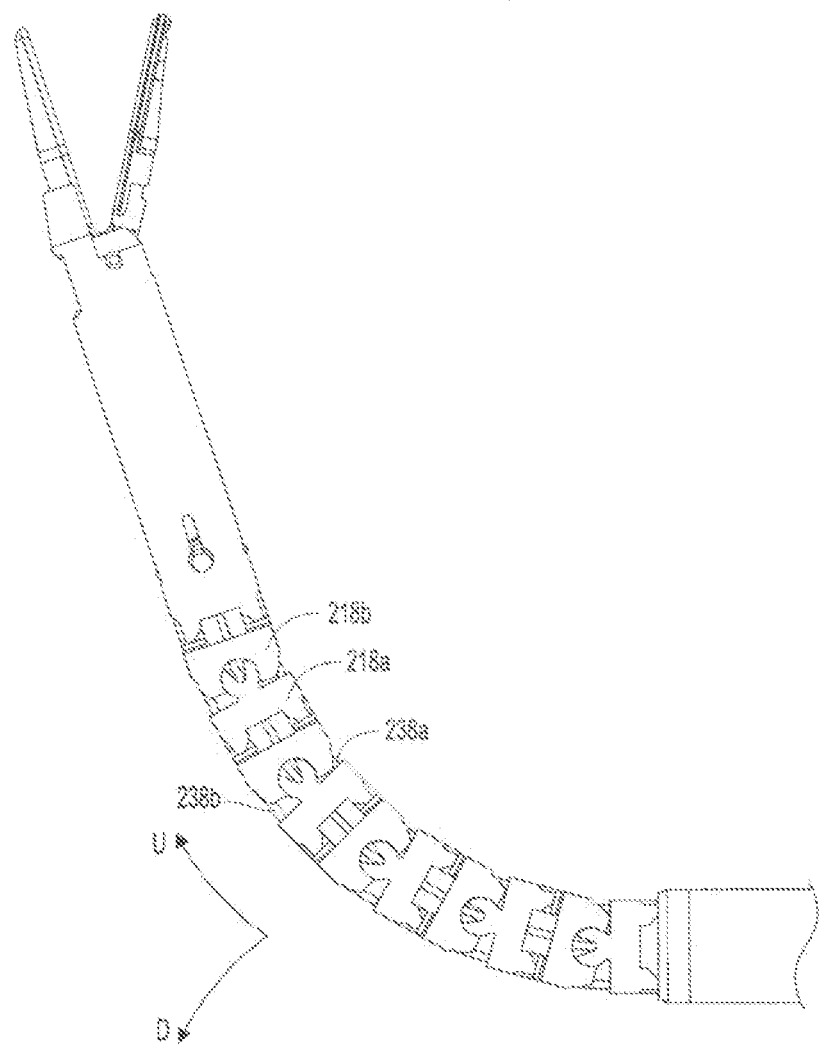
FIG. 16 is an enlarged side view of the flexible shaft and end effector of FIG. 14 in an upwardly articulated position.
Figure 17:
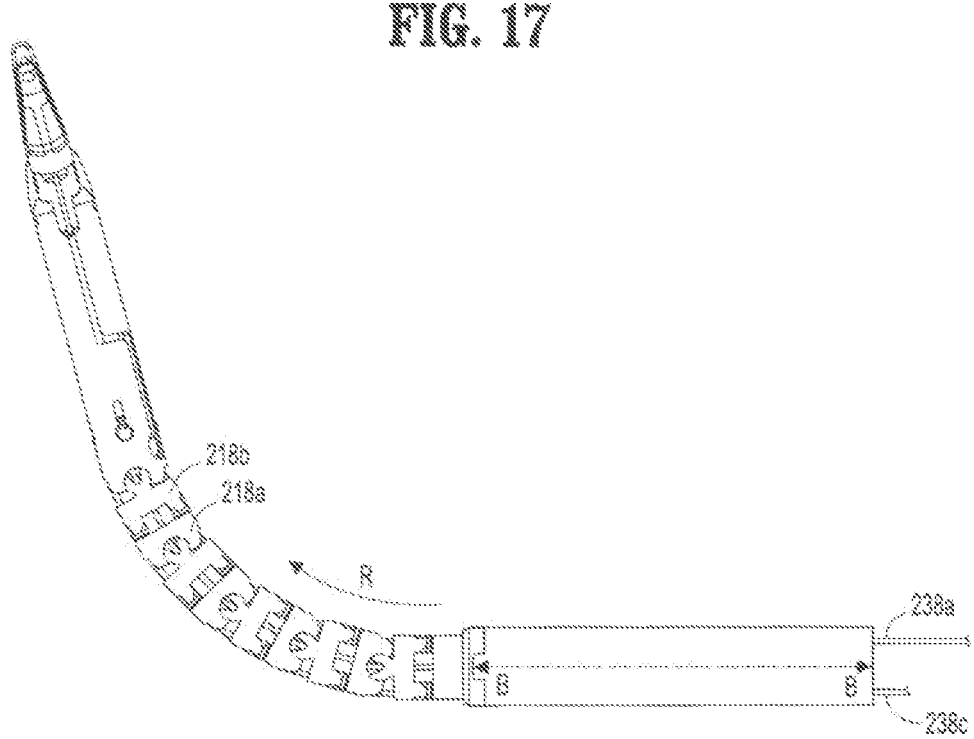
FIG. 17 is an enlarged side view the flexible shaft and end effector of FIG. 14 in a rightward articulated position.
Figure 18:
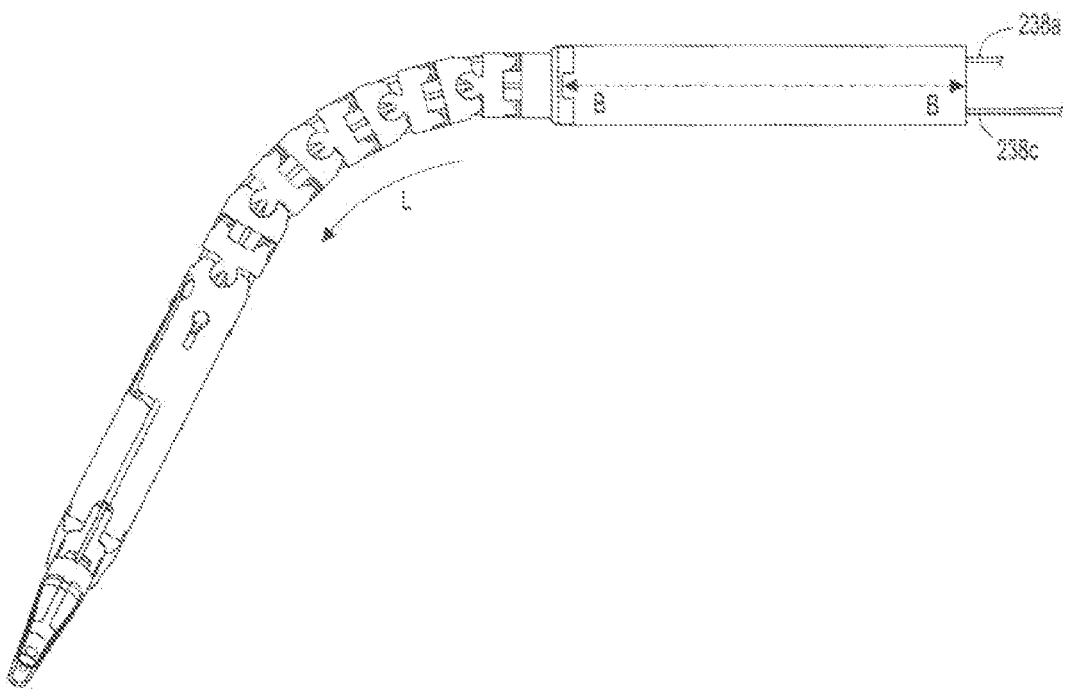
FIG. 18 is an enlarged side view the flexible shaft and end effector of FIG. 14 in a leftward articulated position.

Links 218a are similar in construction to links 218b in that each link 218a, 218b exhibits a pair of distal knuckles 218c and pair of opposing proximal devises 218d formed therewith. Links 218a, however, are oriented with a ninety degree) (90° radial offset with respect to the neighboring link 218b. Such an alternating orientation of the links 218a, 218b facilitates articulation of the end effector 212 in orthogonal planes. The horizontal knuckles 218c of links 218a define a horizontal pivot axis P1. Thus a knuckle 218c of a link 218a operatively engages a corresponding clevis 218d of a neighboring link 218b to facilitate articulation of the end effector 212 in the direction of arrows "U, D" (FIG. 16). Similarly, the knuckles 218c of links 218b define a vertical pivot axis P2 such that a knuckle 218b operatively engages a corresponding clevis 218d of a neighboring link 218a to facilitate articulation of the end effector 212 in the direction of arrows "R, L" (as shown in FIGS. 17, 18)

Each link 218a and 218b includes a central lumen 218e extending longitudinally therethrough. The central lumen 218a permits passage of various actuators, e.g., drive rod 246 and knife rod 250, and other components through the elongated shaft 216. Links 218a, 218b also define two pairs of opposed lumens 218f and 218g formed radially outward from the central lumen 218e. Each of the lumens 218f and 218g on a link 218a is radially spaced at a 90° from the neighboring lumen 218f and 218g such that each lumen 218f aligns with a lumen 218g of a neighboring link 218b. The lumens 218f and 218g cooperate to define a longitudinal cavity to permit passage of four steering cables 238a, 238b, 238c, and 238d through the articulating portion 218 of the elongated shaft 216. A differential tension may be imparted to the four steering cables 238a-d to adjust the orientation of the articulating portion 218 of shaft 216 as described below.

A link support 402 includes a pair of distal knuckles 218c oriented similarly to a link 218a to interface with a trailing link 218b. A proximal end of the link support 402 may be fixedly mounted to an outer casing 400, which in one embodiment extends only over the proximal portion 220 of the elongated shaft 216, however, in a further embodiment, the outer casing 400 extends over both the proximal portion 220 and the articulating portion 218 of the shaft 216. The outer casing 400 is generally flexible to permit the proximal portion 220 to flex and bend freely. An end effector support 404 may include a pair of clevises 218d on a proximal end oriented similarly to the clevises on link 218a to receive the knuckles 218c of a leading link 218.

The four steering cables 238a-d may be substantially elastic and slideably extend through lumens pairs 218f and 218g defined in the links 218a and 218b. A distal end of the each of the steering cables 238a-d is coupled to the end effector support 404. More particularly, each steering cable 238a-d includes a ball-like mechanical interface at the distal end, namely, interfaces 238a'-d'. Each interface 238a'-d' is configured to securely mate within a corresponding recess defined in the end effector support 404. 238a' engages recess 406a, interface 238b' engages recess 406b, and interfaces 238c' and 238d' engage similar recess on the end effector support 404.

The proximal ends of the steering cables 238a-d are operatively coupled to the articulation controls as described below. The steering cables 238a-d extend through the proximal portion of shaft 220 through a series of passageways defined therein. More particularly, a cross-shaped cable guide adapter 408 and guide adapter liner or washer 410 include bores defined therethrough to initially orient the cables 238a-d at 90° degree angles relative to one another for passage into proximal portion of shaft 220. The adapter 408 also facilitates attachment of the proximal portion of shaft 220 to the housing 14 (FIG. 1). The proximal portion of shaft 220 includes passageways 412a-d defined therein to orient the cables 238a-d, respectively, for reception into the lumens 218f, 218g of links 218a and 218b for ultimate connection to the end effector support 404 as described above.

A central guide tube 414 is provided to orient the drive rod 246 and a knife rod 416 through the shaft 216 for ultimate connection to jaw member 240 and a knife 250. The central guide tube 414 may also guide electrical leads 416 providing electrosurgical energy to the jaw member 240, 242. The central guide tube 414 is dimensioned for reception within proximal portion 220 of the shaft 216 310, and may extend distally therefrom into the central lumen 218e defined in the links 218a and 218b. One or more steering cables, e.g., 238a, include a distal portion 238a' that electrically connects to the end effector support 404 which, in turn, connect to jaw member 240. A return path (i.e., ground path) may thus be established through tissue captured between jaw members 240 and 242 for electrosurgical energy provided through jaw member 240.

The central extrusion or guide tube 414 is constructed from a highly flexible and lubricious material and performs several important functions: Guide tube 414 guides the drive rod 246, the knife rod 418 and the electrical lead 416 from the guide adapter 408, proximal portion 220 of shaft 216 and articulating portion 218 to the end effector support 404 and knife 50; the guide tube 414 provides electrical insulation between component parts; the tube 414 keeps the lead 416 and rods 246 and 418 separated during relative movement thereof; the tube 414 minimizes friction and clamping force loss; and tube 414 keeps the lead 416 and rods 246 and 418 close to the central longitudinal axis to minimize stretching during articulation. The tube 414 (and internal lumens) may be made from or include materials like polytetrafluoroethene (PTFE), graphite or other lubricating agents to minimize friction and other common losses associated with relative movement of component parts. Alternatively, a coaxial structure (not shown) may be utilized to guide the drive rod 246 and knife rod 418.

One or more distal guide plates 420 and an adapter 422 may also be utilized to further align the drive rod 246 and knife rod 418 and facilitate actuation of the jaw members 240 and 242. More particularly, alignment of the drive rod 246 facilitates opening and closing the jaw members 240, 242. A sleeve 424 includes an aperture 426 to engage a flange 428 of jaw member 240 such that axial movement of the sleeve 424 forces jaw member 240 to rotate around pivot pin 430 and clamp tissue. Sleeve 424 connects to adapter 422 which secures drive rod 246 therein via a wire crimp 432. The drive rod 246 has a flat at a distal end thereof to reinforce attachment to crimp 432. By actuating movable handle 32 (FIG. 1), the drive rod 246 retracts sleeve 424 to close jaw member 240 about tissue. Pulling the sleeve 424 proximally closes the jaw members 240 and 242 about tissue grasped there between and pushing the sleeve 424 distally opens the jaw members 240 and 242 for grasping purposes. The end effector 212 is designed as a unilateral assembly, i.e., jaw member 242 is fixed relative to the shaft 216 and jaw member 240 pivots about a pivot pin 430 to grasp tissue. Other features of the jaw members 242, 240, their construction and method of manufacturing, their electrical connection and insulative properties, the use of a knife channel, and the methods of maintaining a proper gap are similar to those methods discussed above with respect to the two-wire control systems and are incorporated in connection with the features of the four-wire design as if restated fully here.

Having described herein various aspects of both a two-wire and a four-wire articulation system for use in endoscopic device 10, the following description is generally related to a motorized control system for effectively enabling one handed operation of the electrosurgical device. Such operation should include one handed grasping of tissue, articulation of the end effector in at least two planes, activating the use of electrosurgical energy, and where appropriate the activation of a knife for severing of tissue sealed by the electrosurgical energy.

Figure 19:
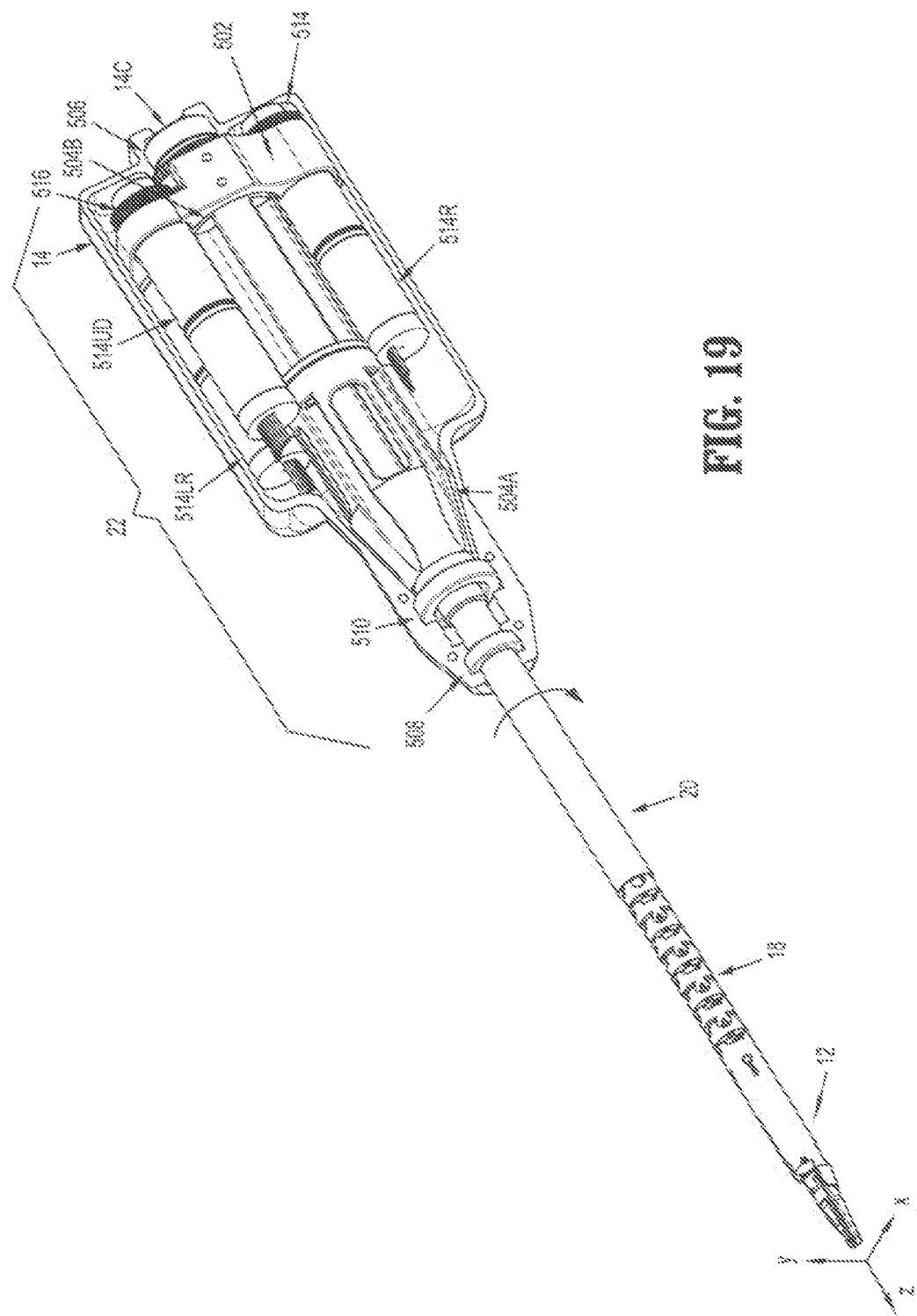
FIG. 19 is a front perspective view of a shaft and steering unit of FIG. 1, with the steering unit cutaway to show the internal mechanism.
Figure 20:
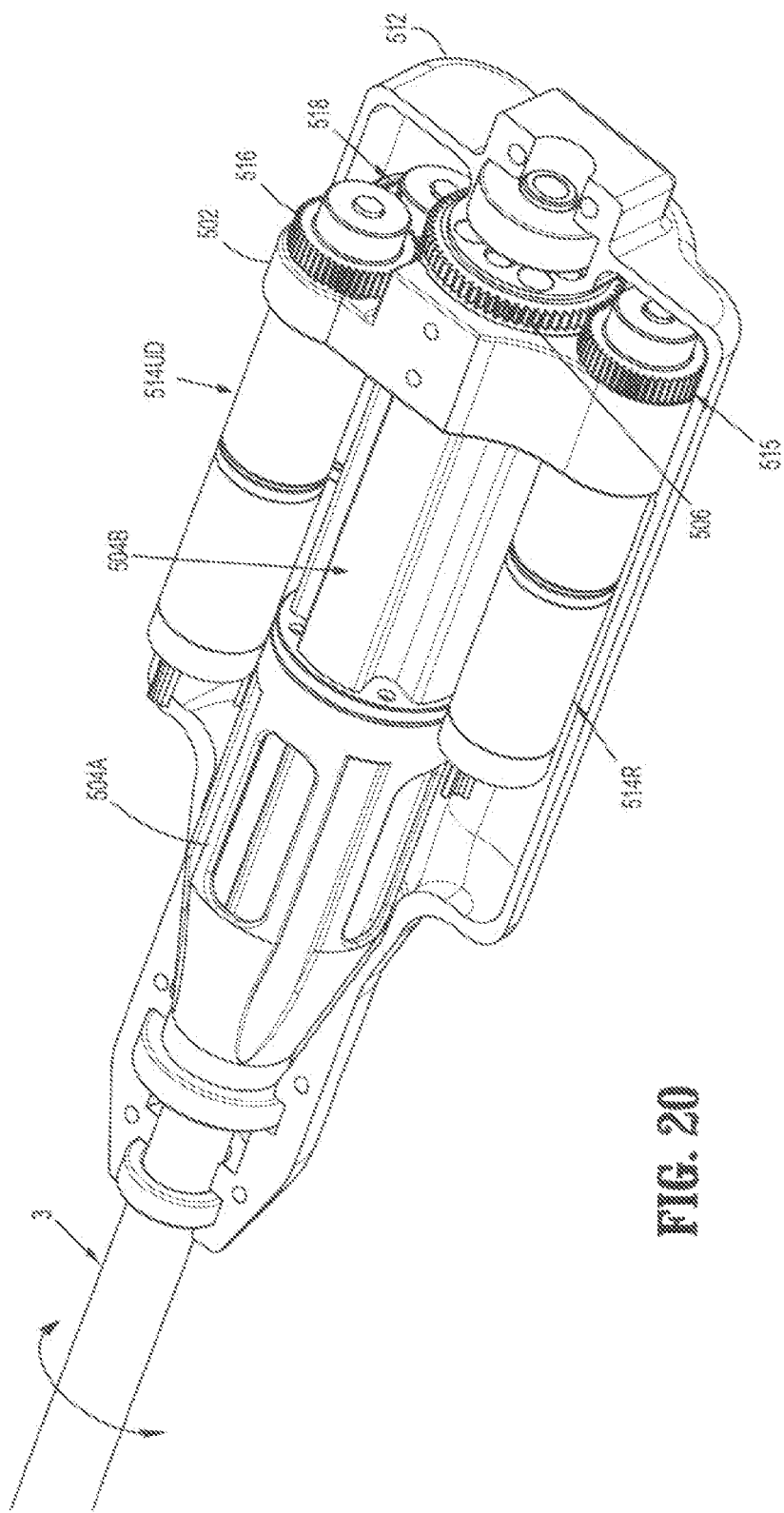
FIG. 20 is a rear perspective view of a portion of a shaft and steering unit of FIG. 1, with the steering unit cutaway to show the internal mechanism.

As noted above, FIG. 1 depicts a steering unit 22. FIG. 19 shows the main components of steering unit 22. The steering unit 22 is housed in housing or body 14 and is mounted on a bracket 502 which integrally connects to the housing or body 14. The shaft 20 connects to and in one embodiment forms an integrated unit with internal casings 504a and 504b, and connects to a spur gear 506. This integrated unit is, in one embodiment rotatable in relation to the housing 14, such that the shaft 20, internal casings 504a-b, and spur gear 506 can rotate about shaft axis "z". The shaft 20 and integrated internal casings 504a-b are supported radially by bearings 508, 510, and 512.

An electric motor 514R, in one embodiment, includes an encorder for converting mechanical motion into electrical signals and providing feedback to the control system 24. Further, the electric motor 514R (R indicates this motor if for inducing rotation of the shaft 20 and end effector 12) may include an optional gear box for increasing or reducing the rotational speed of an attached spur gear 515 mounted on a shaft driven by the electric motor 514R. Electric motors 514LR (LR referring to left-right movement of the articulating portion 18) and 514UD (referring to up-down movement of the articulating portion 18), each optionally includes an encoder and a gearbox. Respective spur gears 516 and 518 drive up-down and left-right steering cables, as will be described in greater detail below. All three electric motors 514 R, LR, and UD are securely attached to the stationary frame 502, to prevent their rotation and enable the spur gears 515, 516, and 518 to be driven by the electric motors.

Figure 21:
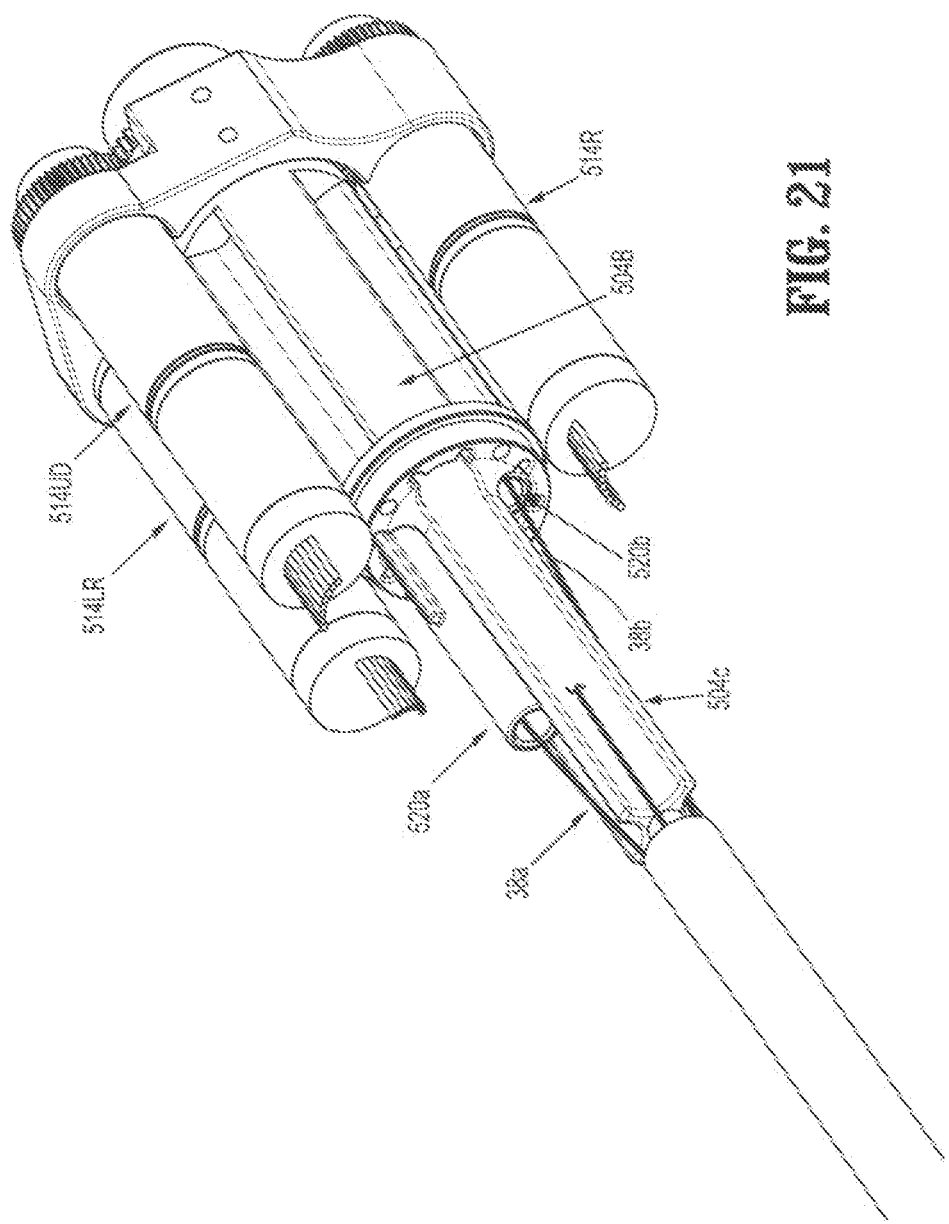
FIG. 21 is a front perspective view of a portion of a shaft and steering unit of FIG. 1, with the steering unit, cutaway to show the internal mechanism and the first casing removed to show its internals.
Figure 22:
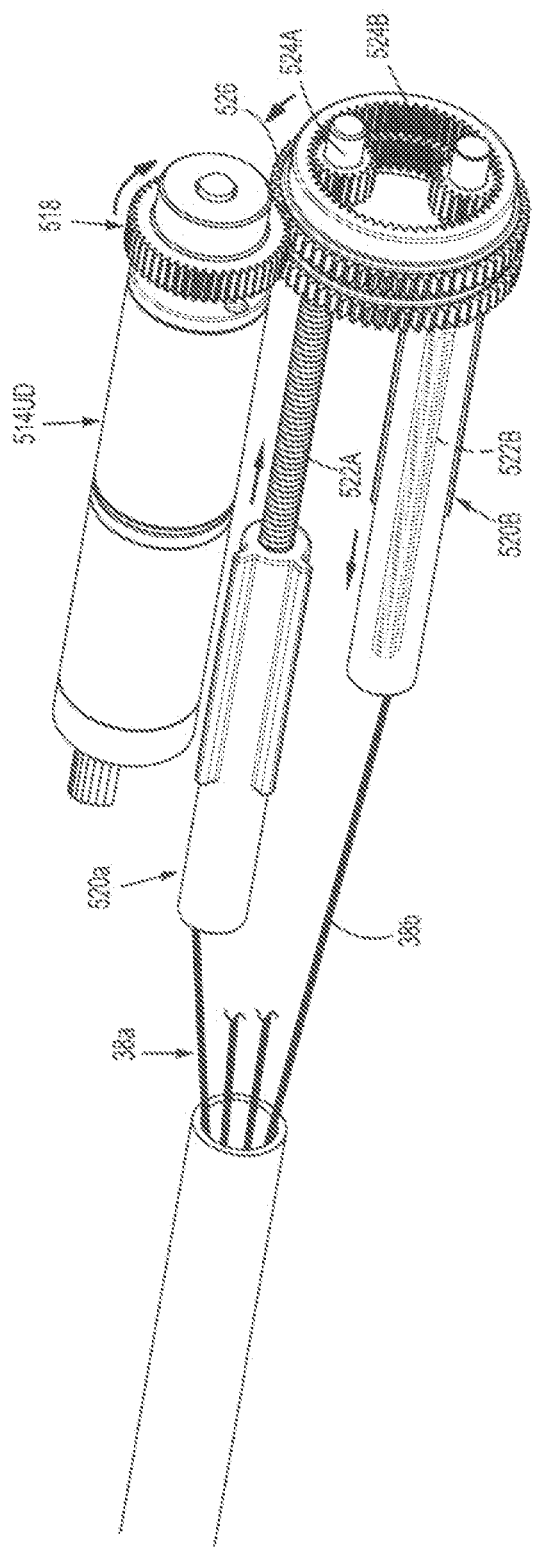
FIG. 22 is a rear perspective view of a motor and planetary gearing of FIG. 1 for driving steering cables.

FIGS. 21 and 22 depict details of the mechanism causing articulating portion 18, and therewith the end effector 12 to articulate. Specifically, the following depicts the manner in which the up-down articulation is contemplated in one aspect of the invention. Such a system alone, coupled with the electric motor 514UD for driving the spur gear 506 would accomplish articulation as described above in a two-wire system. However, where a four-wire system is contemplated, a second system identical to that described immediately hereafter, can be employed to drive the left-right cables. Accordingly, for ease of understanding just one of the systems is described herein, with the understanding that one of skill in the art would readily understand how to employ a second such system in a four-wire system.

To accomplish up-down articulation of the articulating portion 18 and therewith the end effector 12, as in the systems described above, steering cables 38a-b, 138a-b, or 238a-b may be employed. For ease of understanding, the following will only reference one of the articulation systems described above, but any of they may be employed herein without departing from the scope of the present invention. The distal ends of the steering cables 38a-b are attached to, or at, or near the proximal end of the end effector, by the means described above. The proximal ends of the steering cables 38a-b are attached to the distal tips of the posts 520a, and 520b. As shown in FIG. 21, the posts 520a and 520b reciprocate longitudinally, and in opposing directions. Movement of the posts 520a causes one steering cable 38a to lengthen and at the same time, opposing longitudinal movement of post 520b causes cable 38b to effectively shorten. The combined effect of the change in effective length of the steering cables 38a-b is to cause joints 18a forming the articulating portion 18 of shaft 16 to be compressed on the side in which the cable 38b is shortened, and to elongate on the side in which steering cable 38a is lengthened. This is effectuated by the integrated knuckles and devises describe above.

The posts 520a-b slide on an internal frame 504c formed internally to and integrally with casing 504a. Both the internal frame 504c and the posts 520 are preferably formed of a resilient, non-binding, low friction material of the type described herein above to promote efficient and smooth travel of the posts 520a-b along the corresponding and cooperating portions of the internal frame 504c.

The opposing posts 520a and 520b have internal left-handed and right-handed threads, respectively, at least at their proximal ends. As shown in FIG. 22. housed within casing 504b are two threaded shafts 522a and 522b, one is left-hand threaded and one right-hand threaded, to correspond and mate with posts 520a and 520b. The shafts 522a and 522b have distal ends which thread into the interior of posts 520A and 520B and proximal ends with spur gears 524a and 524b.

The shafts 522a and 522b have freedom to rotate about their axes. The spur gears 524a and 524b engage the internal teeth of planetary gear 526. The planetary gear 526 also an external teeth which engage the teeth of spur gear 518 on the proximal end of electric motor 514UD.

To articulate the end effector 12 in the upwards direction, a user or surgeon activates via the activation switch 30 the electric motor 514UD causing it to rotate the spur gear 518, which in turn drives the planetary gear 526. The planetary gear 526 is connected through the internal gears 524a and 524b to the shafts 522a and 522b. The planetary gear 526 will cause the gears 524a and 524b to rotate in the same direction. The shafts 522a and 522b are threaded, and their rotation is transferred by mating threads formed on the inside of posts 520a and 520b into linear motion of the posts 520a and 520b. However, because the internal threads of post 520a are opposite that of post 520b, one post will travel distally and one will travel proximally (i.e., in opposite directions) upon rotation of the planetary gear 526. Thus the upper cable 38a is pulled proximally to lift the end effector, while the lower cable 38b must be relaxed. As stated above, this same system can be used to control left-right movement of the end effector, using the electric motor 514LR, its spur gear 516, a second planetary gear 526, and a second set of threaded shafts 522 and posts 520 and two more steering cables 38. Moreover, by acting in unison, a system employing four steering cables can approximate the movements of the human wrist by having the three electric motors 514 and their associated gearing and steering cables 38 computer controlled by the control unit 24. Such a system is described in greater detail below.

In use, if the end effector 12 has been articulated such that it is in the up position, e.g., bent approximately 90° from its longitudinal axis, and then the electric motor 514R is energized, then shaft 3 will rotate and the articulated tip will start moving to the left or right position of its original position. In some instances such a rotation will be desirable to the surgeon. However, in other situations it will not be desirable, or in the performance of more complicated maneuvers there will be a desire to maintain some aspect of the end effector's position and enable wrist-like movement of the articulating portion 18 without changing the orientation of the end effector 12, perhaps to enable some subsequent action that depends upon repositioning of the articulating portion 18 before it can be performed. To accomplish this aspect of the present disclosure the actions of all three electric motors 514R, LR, and UD must be synchronized by the control system 24.

In the synchronized mode, when the motor 514R rotates the shaft 3 by specific angular increment, this increment is identified by the motor encoder and is sent to the control unit 24. The control unit 24 calculates correction increments and orders the motors 514UD, 514LR to tension and relax as necessary their respective steering cables 38 such that the end effector 12 remains in the up position while the articulating portion rotates to a desired position, defined by the total rotation of the motor 514R.

As described above, the control unit 24 contains a processing unit, (e.g., a microcontroller), a user interface through which the surgeon specifies the desired action and a motor interface. The user interface receives user commands from activation switch 30, which may be a directional button, a joystick such as a thumb operated joystick, a toggle, a pressure sensor, a switch, a trackball, a dial, a optical sensor, and any combination thereof. The processing unit responds to the user commands by sending control signals to the motors 514. The encoders of the motors 514 provide feedback to the processing unit 24 about the current status of the motors 514.

An algorithm, employed to maintain the position of the end effector 12 while rotating the shaft 16 is incorporated into software stored in a memory portion of the of control unit 24. Thus the end effector 12 can be wrist rotated by applying different motor positions of the steering cables in the orthogonal planes.

Multiple plane articulation and rotation controlled by independent step motors, as described above, can result in a number of tip motions, all of which can be synchronized by the control system 24, which may be for example a microprocessor. To clarify the types of motions possible it is useful to consider an additional coordinate system.

Figure 23:
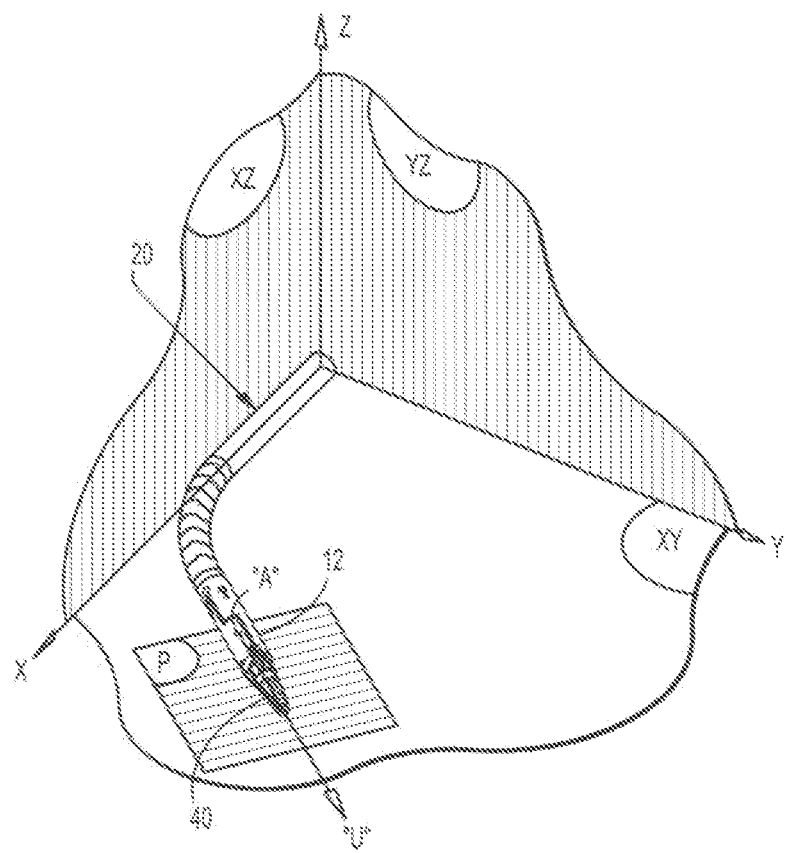
FIG. 23 is a perspective view of a shaft according to one aspect of the present disclosure depicting reference coordinate systems and planes.

As depicted in FIG. 23, the first system XYZ is stationary with axis X substantially aligned with the center axis of non-articulating portion 20 of the shaft 16. Additionally shown is a plane P aligned with the clamping surface of the stationary jaw 42 of the end effector 12, the point is A located on the center axis of the end effector 12, and the axis "U" is aligned with the center axis of the end effector 12.

In operation, the motor 514LR acting independently can articulate the end effector 12 to the left or right in the XY plane with the plane P (and the clamping surface of the stationary jaw 42) substantially orthogonal to a plane XZ. The motor 514UD, acting independently, can articulate the end effector 12 up and down in the plane XZ with the plane P substantially orthogonal to the plane XZ. Thus, operating the motors 514UD and 514LR independently the user can articulate the tip to desired position in the 3D space with the plane P generally oriented orthogonally to the plane XZ.

However, synchronized 3D articulation of the end effector 12, when driven by motors 514UD and 514LR simultaneously (or in a coordinated fashion) and controlled by the control system 24 microprocessor, allows movement of the end effector 12 such that the tip can move along prescribed path. For example the tip can articulate along a circle in CCW direction, with the plane P still generally normal to XZ.

Alternatively, the synchronized motion can incorporate rotational motion imparted by motor 514R which rotates the articulated shaft 16 CW. According to one aspect of the present disclosure, the motors 514UD and 514 LR can simultaneously (or in a coordinated fashion) articulate the end effector 12 CCW, in the manner described above, to negate the rotational motion. As the result, point A of the end effector 12 will stop moving, however, the end effector 12 as well as the plane P and flat surface of the stationary jaw 42 will rotate around axis "U." This motion called wrist-rotation allows the user to rotate the jaws in chosen articulated position. Such wrist-rotation is, according to the present disclosure, achieved without mechanical rotational connection of the end effector 12 with respect to the rest of the shaft 16 and eliminates the need for slip rings in this area if electrical energy is to be supplied to the jaws.

Further, by rotating the shaft 16 with the motor 514R (and compensating "back drive" of the reciprocating posts 520 with the synchronized motion of the motors 514UD and 514 LR purely rotational motion of the shaft in which plane P rotates around axis X can be achieved. As can be seen, the proposed system allows wide range of the motion of the distal tip which can be executed in hand held device or robotic arm.

Though disclosed herein with respect to a handheld electrosurgical device, those of skill in the art will readily understand that the methods and mechanism disclosed herein is readily applicable for use as a component in a robotic surgical device wherein the electrosurgical device is held by or incorporated into a remotely operated surgical arm.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument for treating tissue, comprising:
a housing having a shaft extending there from, said shaft including at least an articulating portion and an end effector;
a first casing connected to and rotatable with the proximal end of said shaft;
an internal frame housed within the first casing;
a plurality of posts, supported by the internal frame and connected on their distal ends to at least one drive wire, and connected on their proximal ends to a threaded shaft;
a second casing connected to the first casing and rotatable therewith, said second casing housing the threaded shafts;
a first electric motor driving a first gear, said first gear interfacing with the threaded shafts such that a first pair of the plurality of threaded shaft rotate in a same direction;
a second electric motor driving a second gear, said second gear causing the connected shaft and first and second casings to rotate about a common axis;
wherein driving said first gear in a first direction causes said articulating portion to articulate in a first plane.

* * * * *